US008663294B2

(12) United States Patent
Dutoit et al.

(10) Patent No.: US 8,663,294 B2
(45) Date of Patent: Mar. 4, 2014

(54) APPARATUS AND METHODS FOR VERTEBRAL AUGMENTATION USING LINKED EXPANDABLE BODIES

(75) Inventors: Christof Dutoit, Solothurn (CH); Andreas Appenzeller, Biel (CH); Thierry Stoll, Meinisberg (CH); Robert Frigg, Bettlach (CH); Robert Rauker, Chester Springs, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/572,975

(22) Filed: Aug. 13, 2012

(65) Prior Publication Data
US 2012/0310355 A1 Dec. 6, 2012

Related U.S. Application Data

(60) Continuation of application No. 12/704,421, filed on Feb. 11, 2010, now Pat. No. 8,267,971, which is a division of application No. 11/523,202, filed on Sep. 18, 2006, now abandoned.

(60) Provisional application No. 60/725,773, filed on Oct. 12, 2005, provisional application No. 60/728,442, filed on Oct. 19, 2005, provisional application No. 60/730,909, filed on Oct. 27, 2005, provisional application No. 60/733,026, filed on Nov. 3, 2005, provisional application No. 60/722,064, filed on Sep. 28, 2005, provisional application No. 60/726,835, filed on Oct. 13, 2005, provisional application No. 60/733,647, filed on Nov. 4, 2005, provisional application No. 60/753,782, filed on Dec. 23, 2005, provisional application No. 60/789,956, filed on Apr. 5, 2006, provisional application No. 60/748,377, filed on Dec. 8, 2005.

(51) Int. Cl.
*A61B 17/70* (2006.01)

(52) U.S. Cl.
USPC .................................................. 606/279

(58) Field of Classification Search
USPC ............ 606/76–78, 246, 254–263, 279–300, 606/326–328; 623/17.11–17.16
See application file for complete search history.

(56) References Cited

U.S. PATENT DOCUMENTS 4,611,581 A * 9/1986 Steffee ........................ 606/292
5,370,611 A 12/1994 Niezink et al.
(Continued)

FOREIGN PATENT DOCUMENTS

EP 0621020 10/1994
EP 1308134 7/2003
(Continued)

OTHER PUBLICATIONS

Furderer, et al., "Vertebral Body Stenting," Orthopaede 31:356-361 (2002) (in German, w/English language translation).

(Continued)

*Primary Examiner* — Jan Christopher Merene
*Assistant Examiner* — Steven Cotroneo
(74) *Attorney, Agent, or Firm* — Stradley Ronon Stevens & Young, LLP

(57) ABSTRACT

Implants and methods for osteopathic augmentation and repositioning of vertebrae may comprise a chain having one or more beads or bodies configured for insertion into a vertebral body. The one or more bodies may be expandable. As the chain is inserted into the vertebral body, it may fill a central portion thereof and can push against the inner sides of the endplates of the vertebral body, thereby providing structural support and tending to restore the vertebral body to its original height. The one or more bodies may have a first configuration dimensioned to pass through a catheter or other introducer, and may expand to a second, larger configuration after insertion into the bone in order to secure the chain within the bone.

10 Claims, 24 Drawing Sheets

(56) References Cited

U.S. PATENT DOCUMENTS

| | | | |
|---|---|---|---|
| 5,370,661 A * | 12/1994 | Branch | 606/232 |
| 5,690,678 A | 11/1997 | Johnson | |
| 5,702,454 A | 12/1997 | Baumgartner | |
| 5,782,831 A | 7/1998 | Sherman et al. | |
| 5,878,886 A * | 3/1999 | Marshall | 206/470 |
| 6,235,043 B1 | 5/2001 | Reiley et al. | |
| 6,248,110 B1 | 6/2001 | Reiley et al. | |
| 6,277,120 B1 | 8/2001 | Lawson | |
| 6,325,802 B1 | 12/2001 | Frigg | |
| 6,423,083 B2 | 7/2002 | Reiley et al. | |
| 6,491,714 B1 | 12/2002 | Bennett | |
| 7,351,262 B2 | 4/2008 | Bindseil et al. | |
| 7,771,458 B2 | 8/2010 | Biedermann et al. | |
| 2002/0068974 A1 | 6/2002 | Kuslich et al. | |
| 2002/0143328 A1 | 10/2002 | Shluzas et al. | |
| 2002/0183752 A1 | 12/2002 | Steiner et al. | |
| 2003/0088249 A1 | 5/2003 | Furderer | |
| 2004/0073308 A1 | 4/2004 | Kuslich et al. | |
| 2004/0078080 A1 | 4/2004 | Thramann et al. | |
| 2004/0097930 A1 | 5/2004 | Justis et al. | |
| 2004/0177847 A1 | 9/2004 | Foley et al. | |
| 2005/0131548 A1 | 6/2005 | Boyer et al. | |
| 2005/0278023 A1 | 12/2005 | Zwirkoski | |
| 2006/0089715 A1 | 4/2006 | Truckai et al. | |
| 2006/0095138 A1 | 5/2006 | Truckai et al. | |
| 2006/0100706 A1 | 5/2006 | Shadduck et al. | |
| 2006/0122625 A1 | 6/2006 | Truckai et al. | |

FOREIGN PATENT DOCUMENTS

| | | |
|---|---|---|
| JP | 06154258 | 6/1994 |
| JP | 2003126108 | 5/2003 |
| WO | 0154598 | 2/2001 |
| WO | 2004047689 | 6/2004 |
| WO | 2004086934 | 10/2004 |
| WO | 2004108019 | 12/2004 |
| WO | 2005027734 | 3/2005 |
| WO | 2005092248 | 10/2005 |
| WO | 2005041796 | 12/2005 |

OTHER PUBLICATIONS

Gaitanis, et al., "Balloon Kyphoplasty for the treatment of pathological vertebral compression fractures," Eur Spine 14:250-260 (2005).

Jang, "Pulmonary embolism of polymethylmethacrylate after percutaneous vertebroplasty: a report of three cases," Spine 27(19):E416-E418 (2002).

Lieberman, et al., "Initial outcome and efficacy of kyphoplasty in the treatmetn of painful osteoporotic vertebral compression fractures," Spine 26(14):1631-1638 (2001).

Magerl, et al., "A comprehensive classification of thoracic and lumbar injuries," Eur Spine 184-201 (1994).

Truumees, "Comparing kyphoplasty and vertebroplasty," Advances in Osteoporotic Fracture Management 1(4) (2002).

* cited by examiner

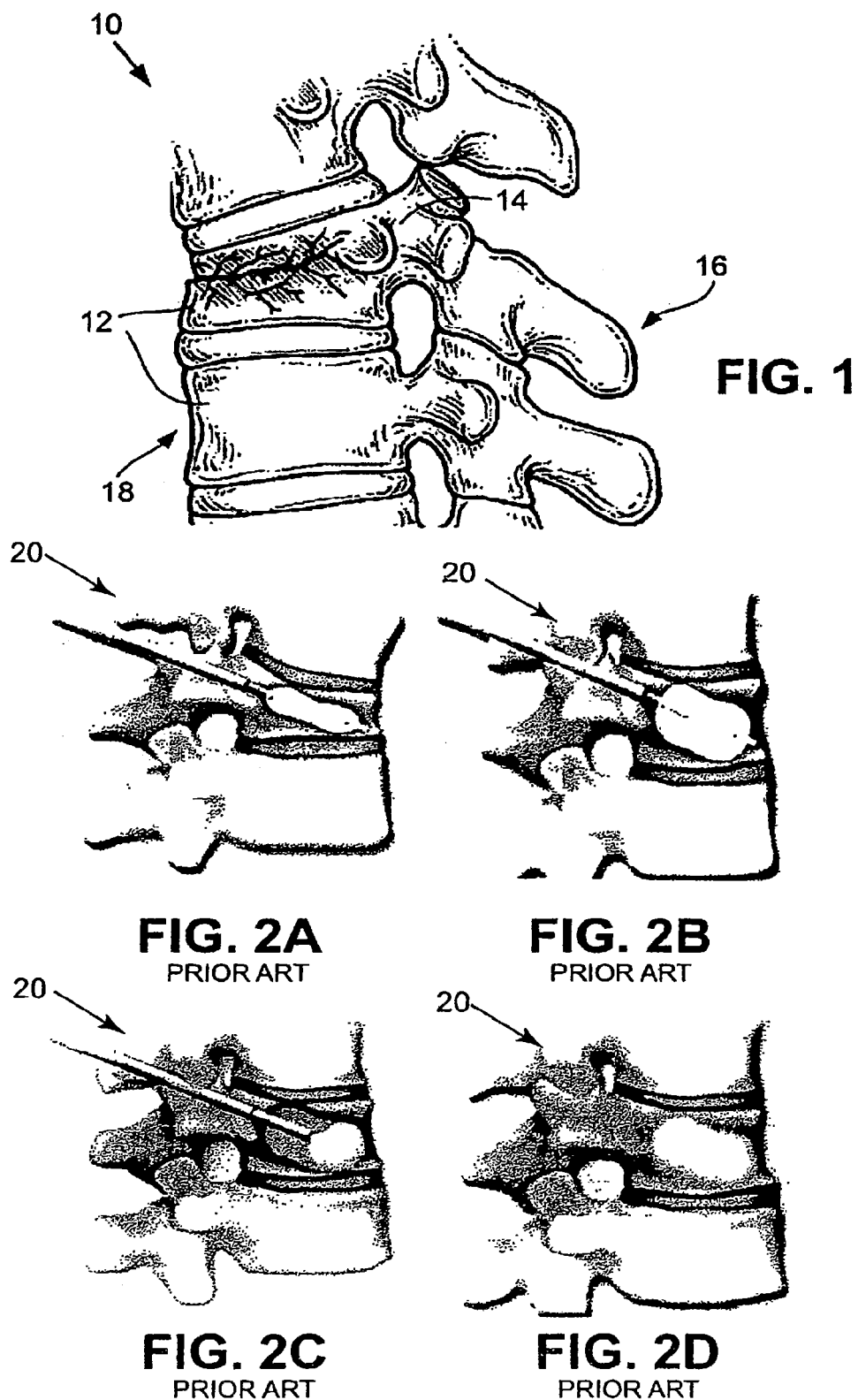

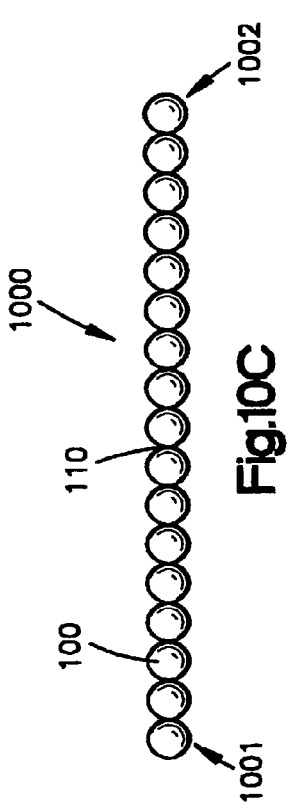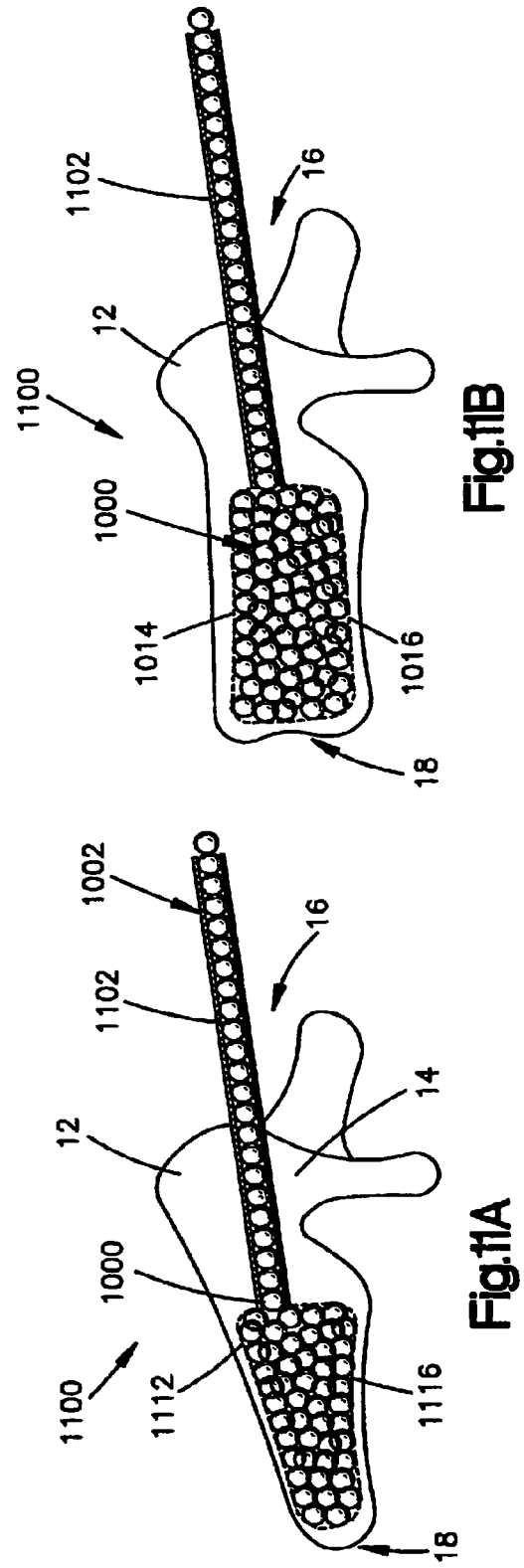

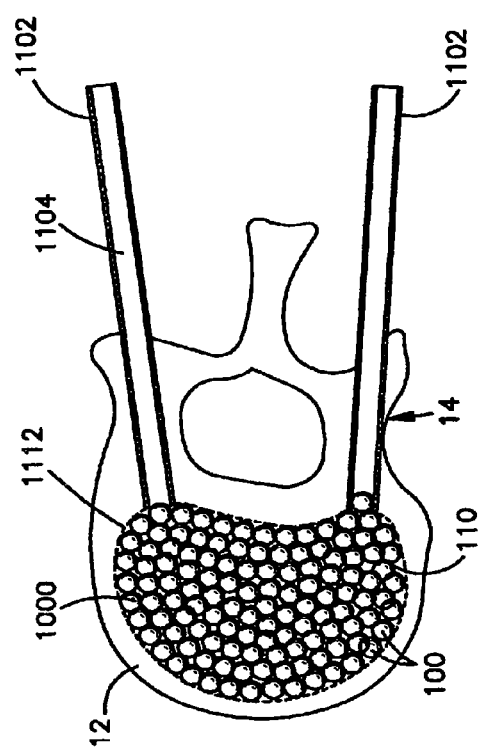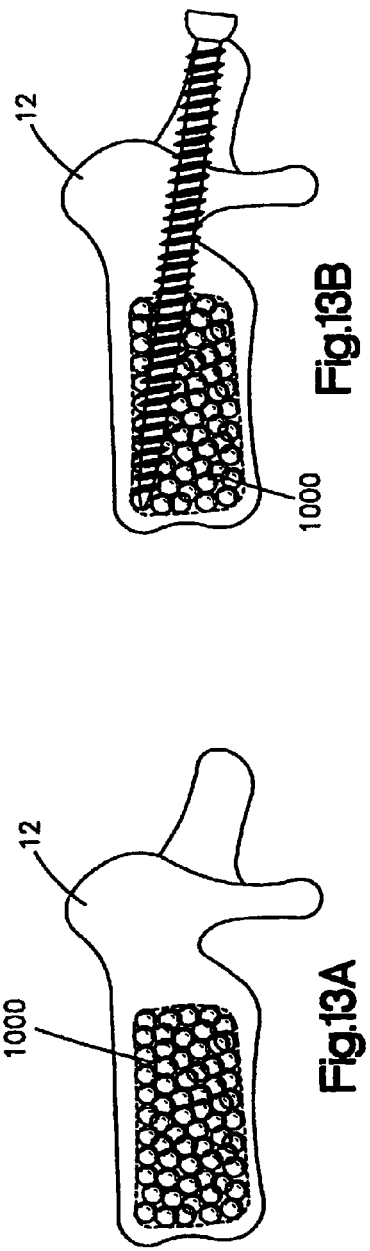

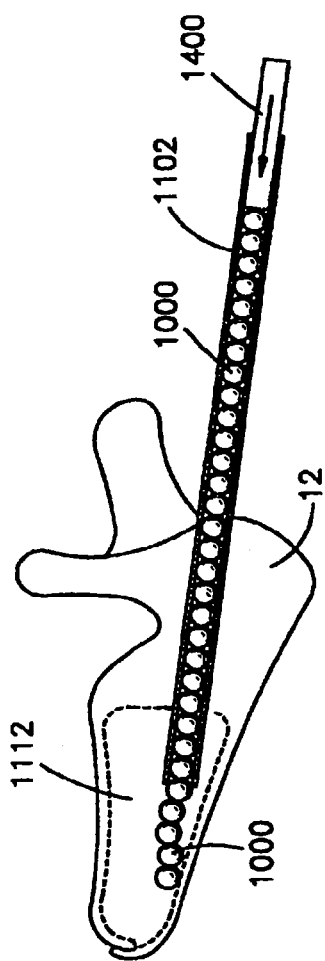
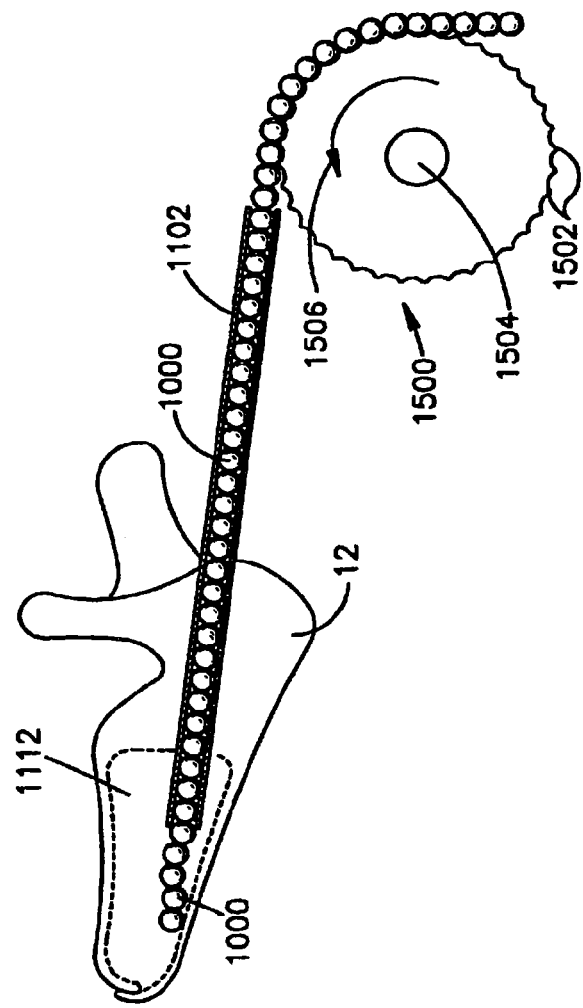

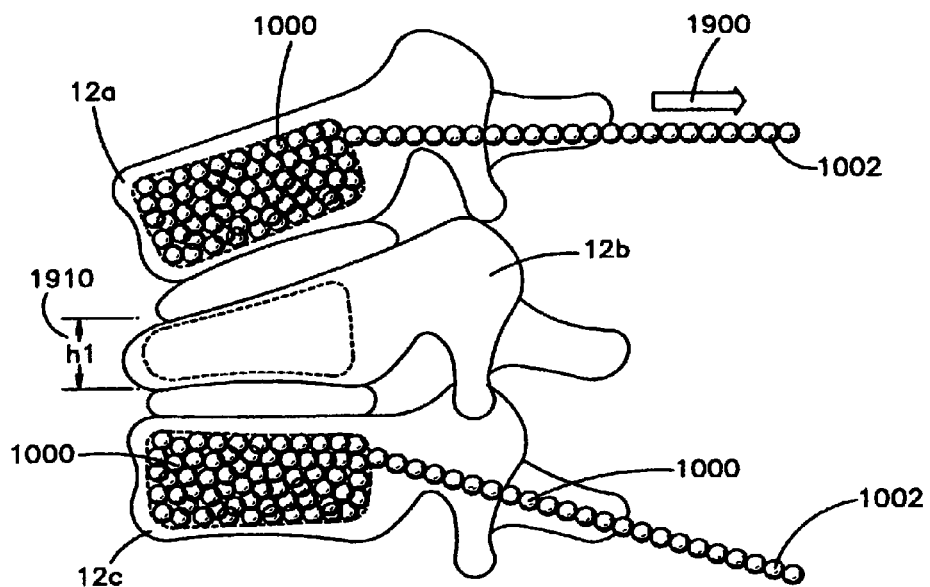
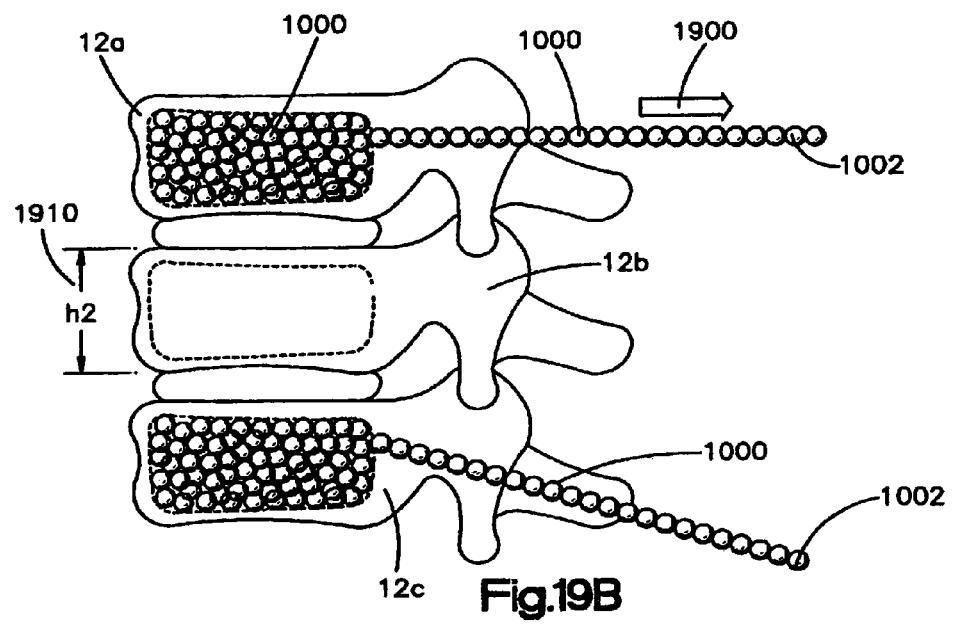

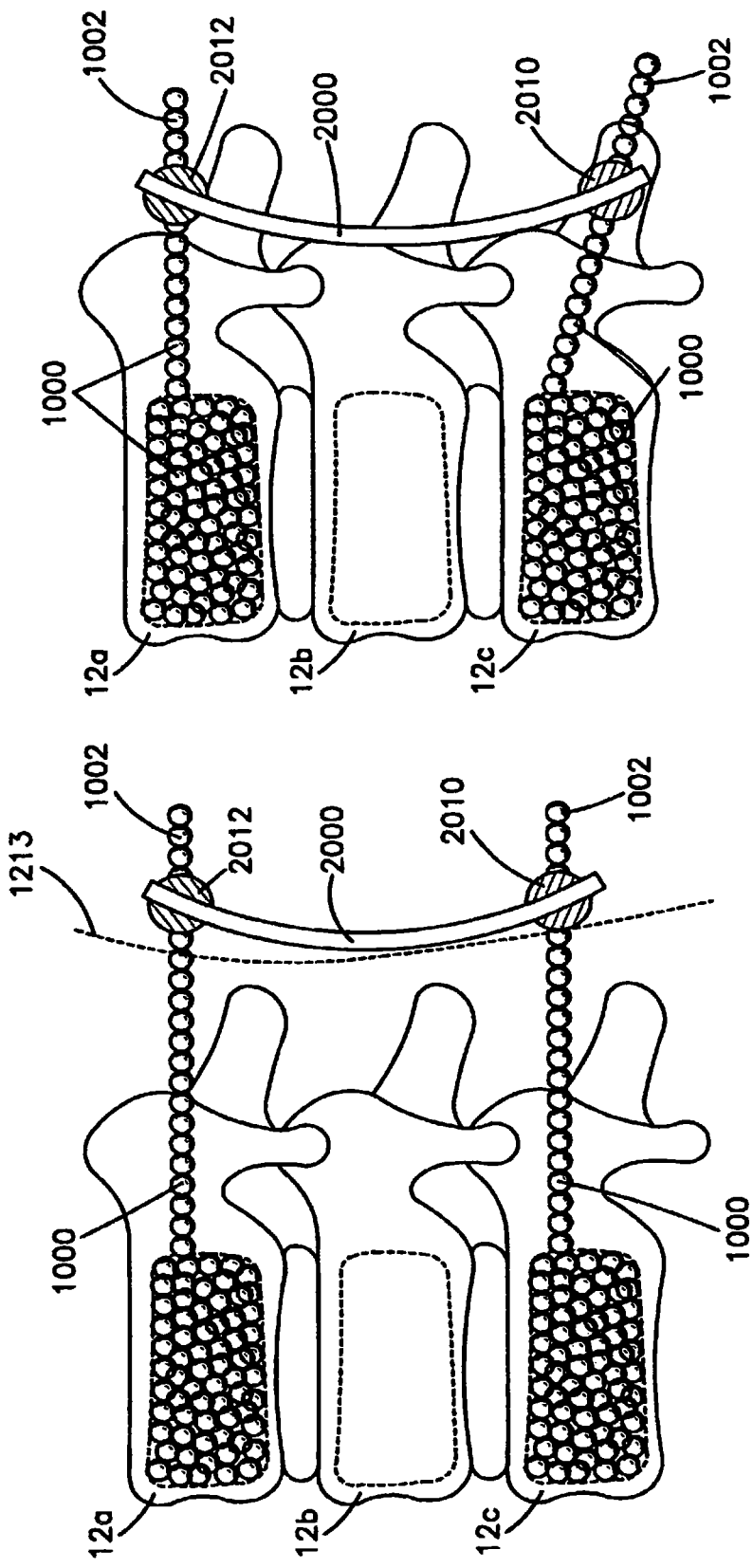

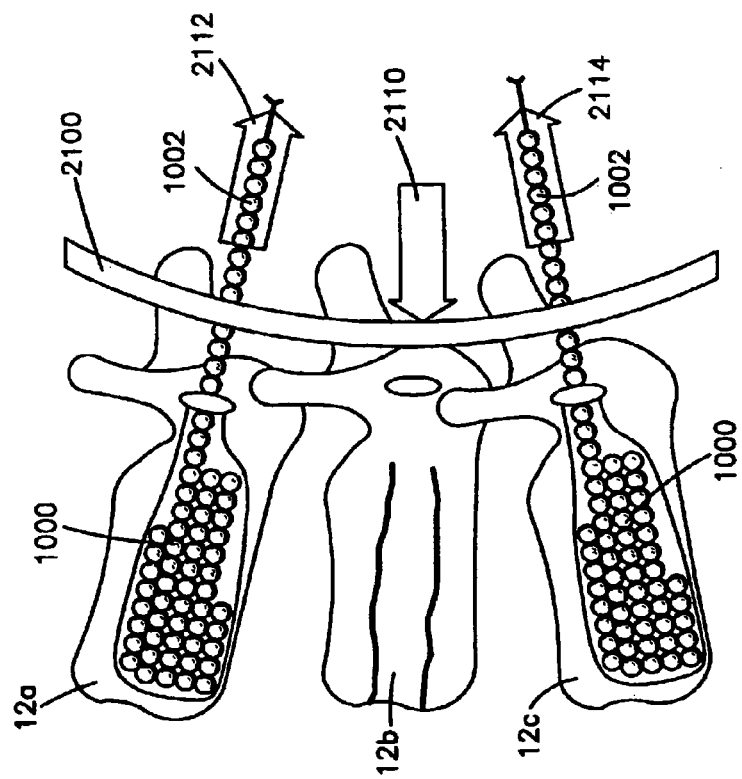
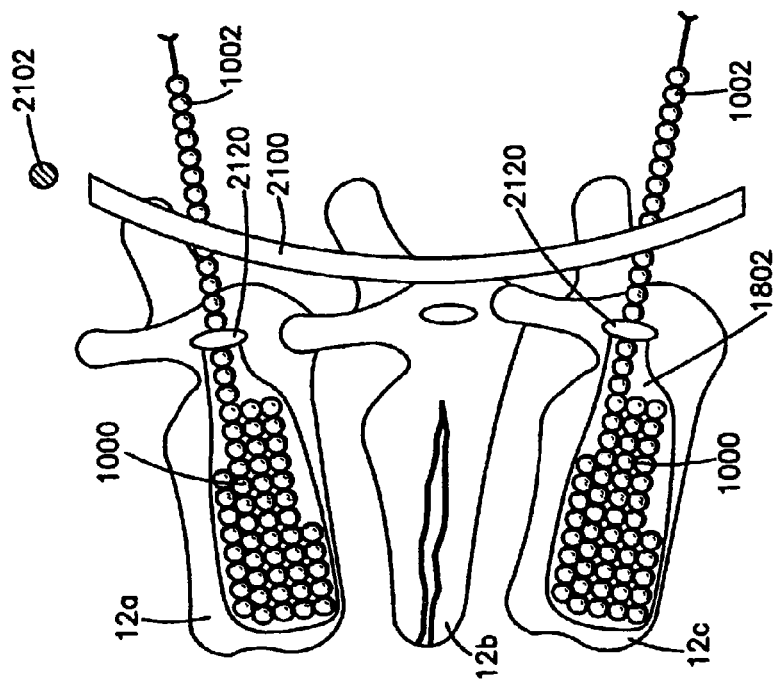

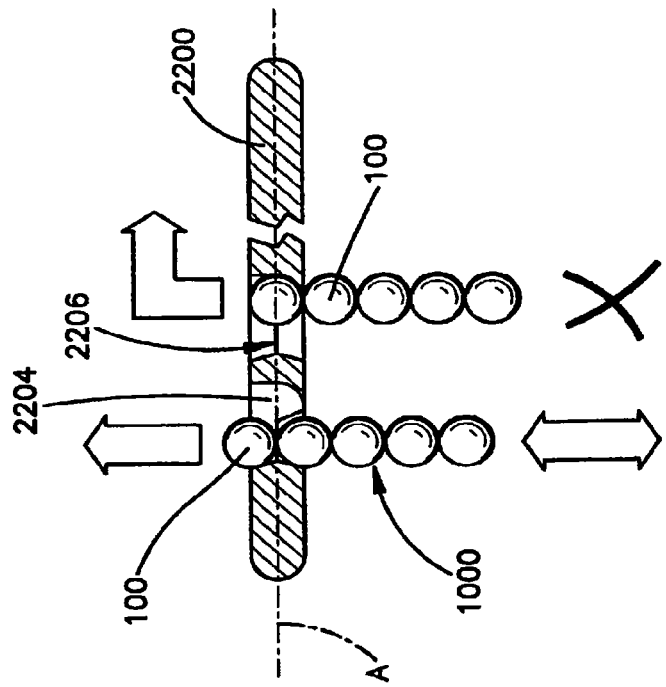
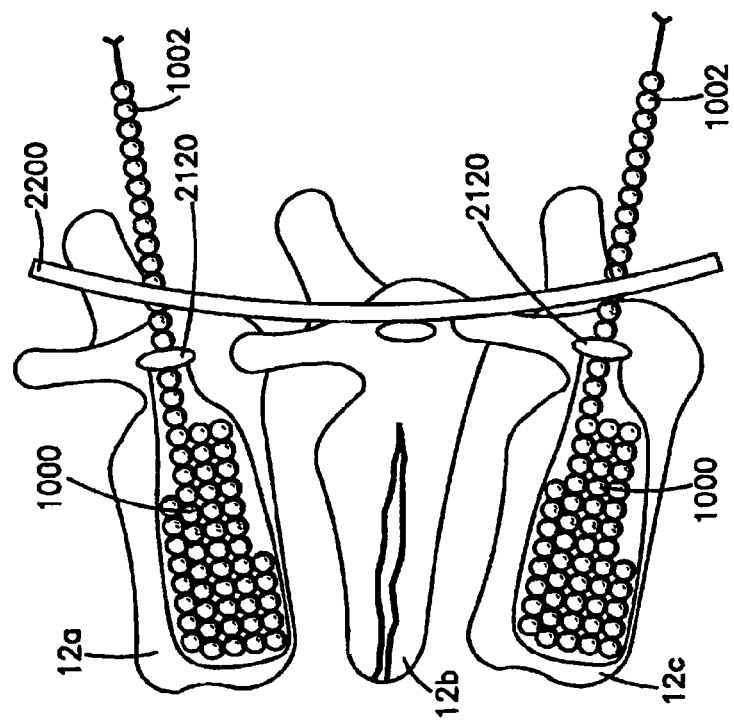

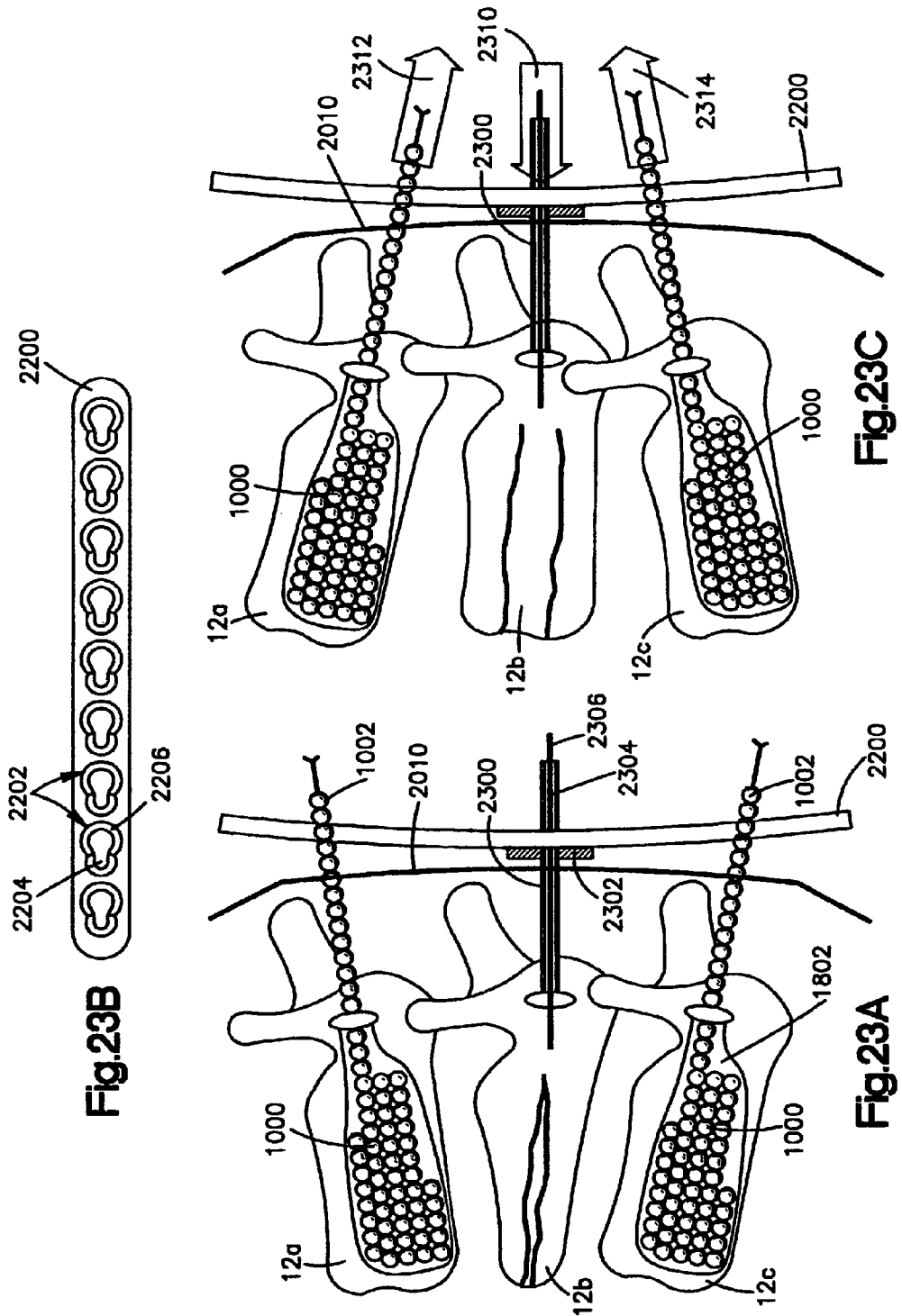

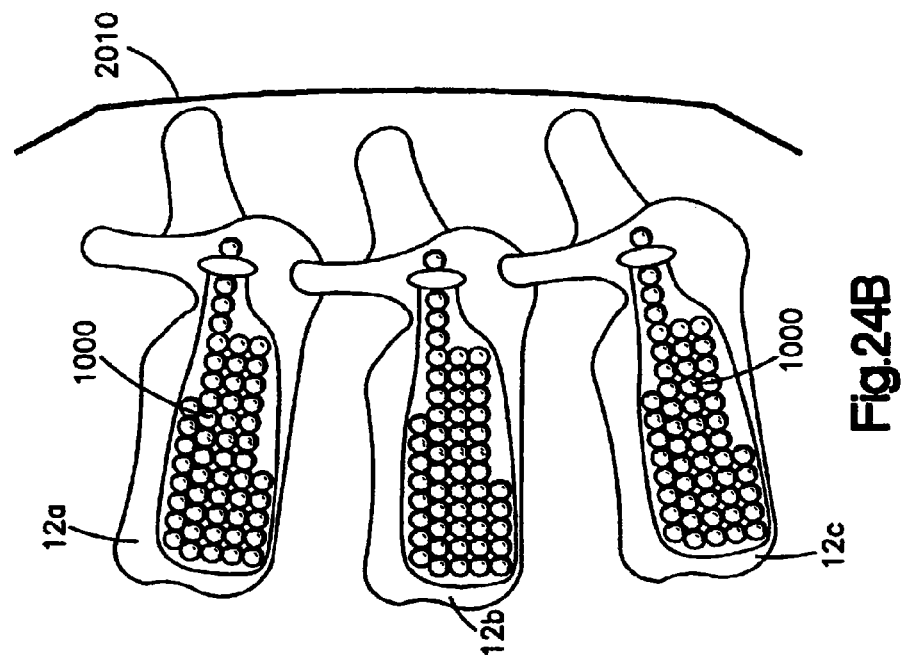
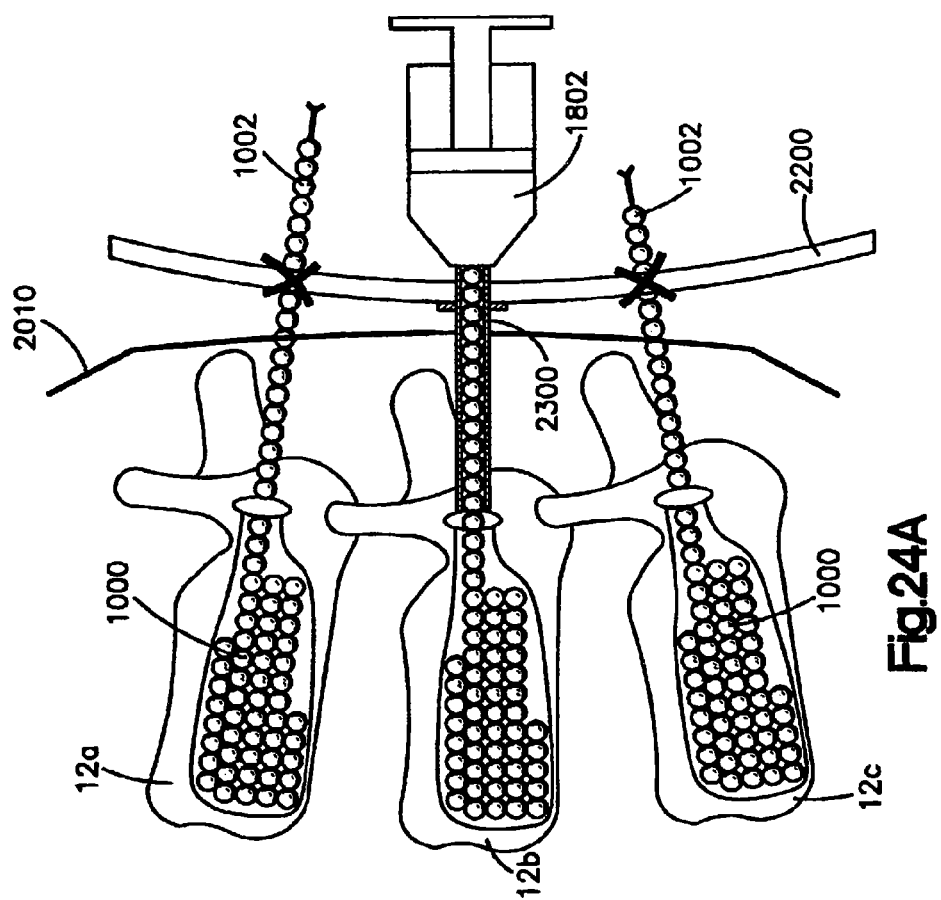

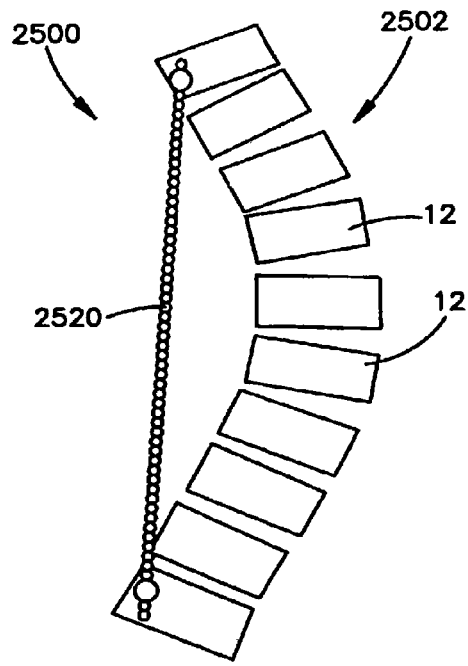
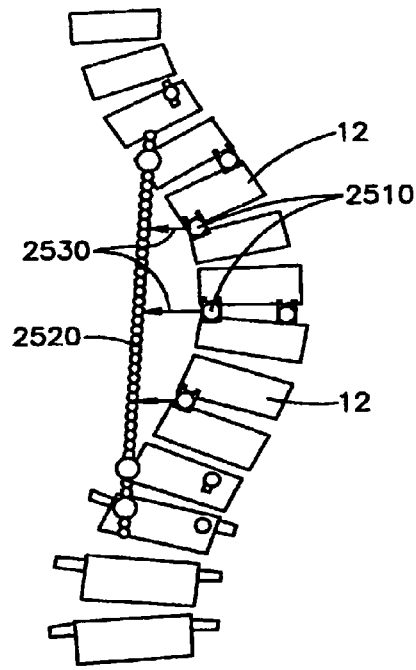
Fig.25A                    Fig.25B
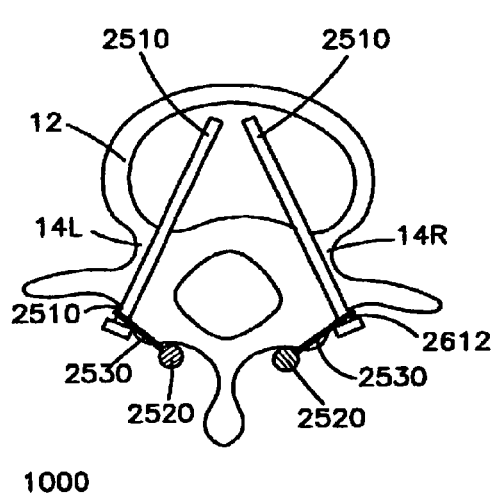
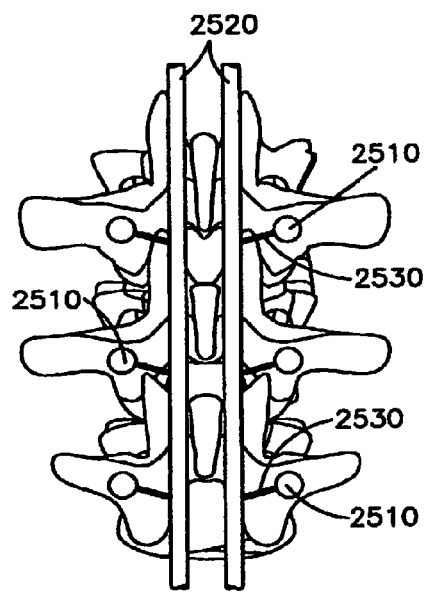
Fig.26A                    Fig.26B

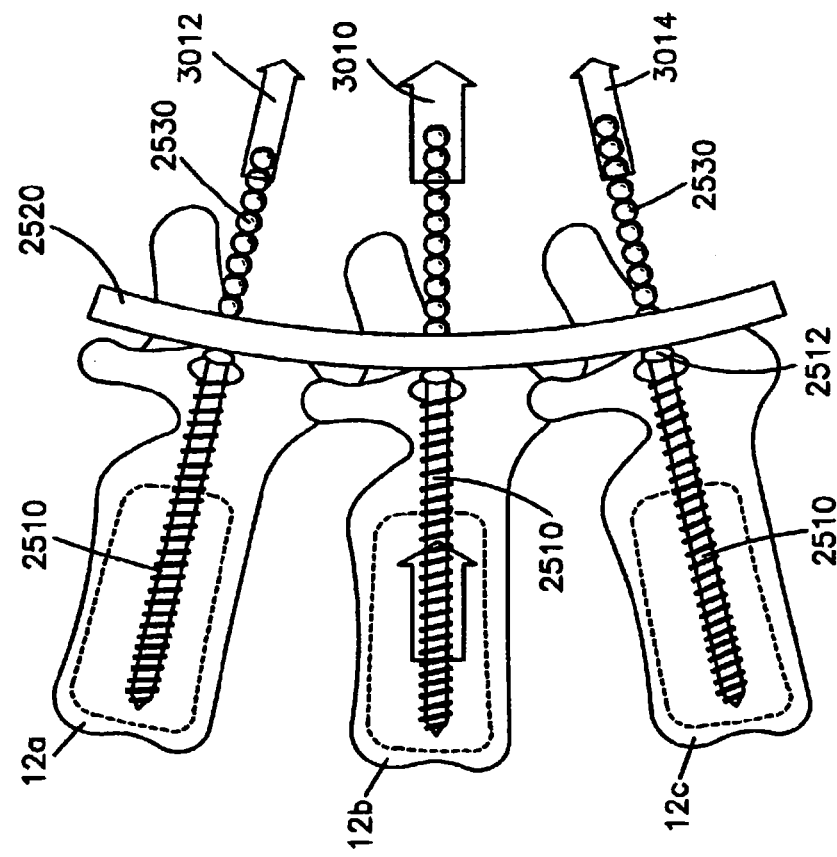
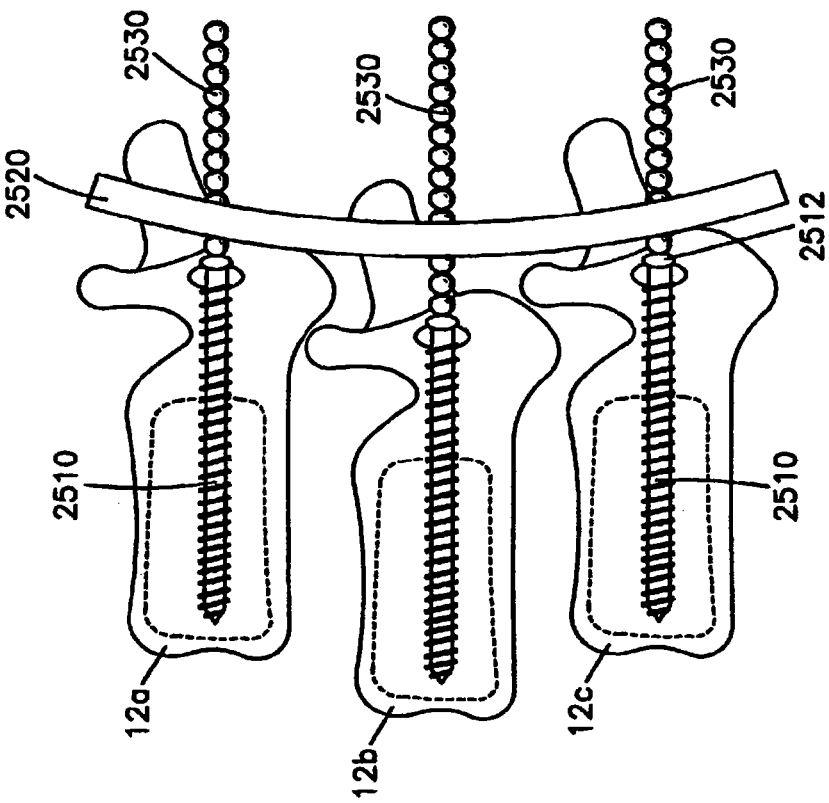
Fig.30A
Fig.30B

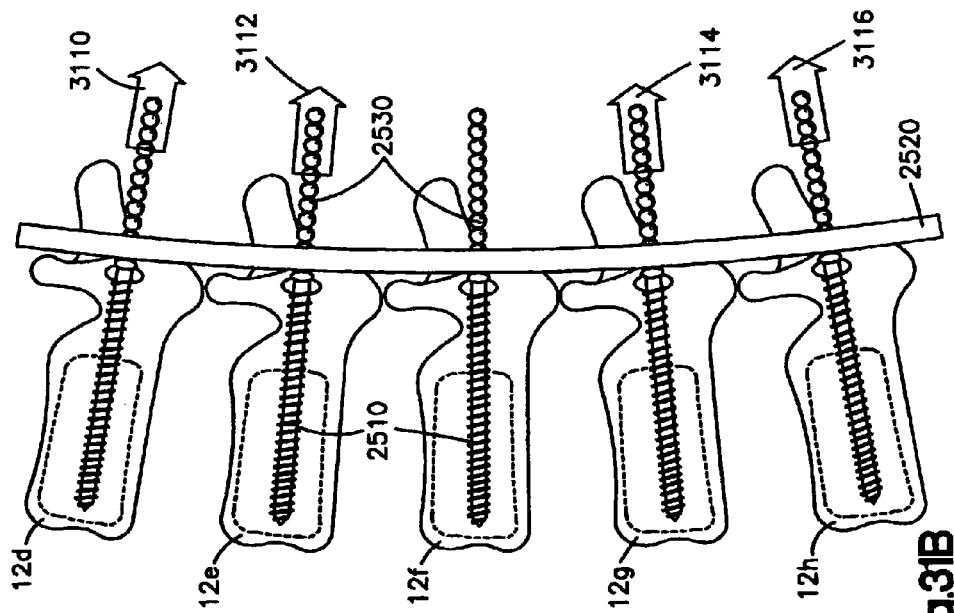
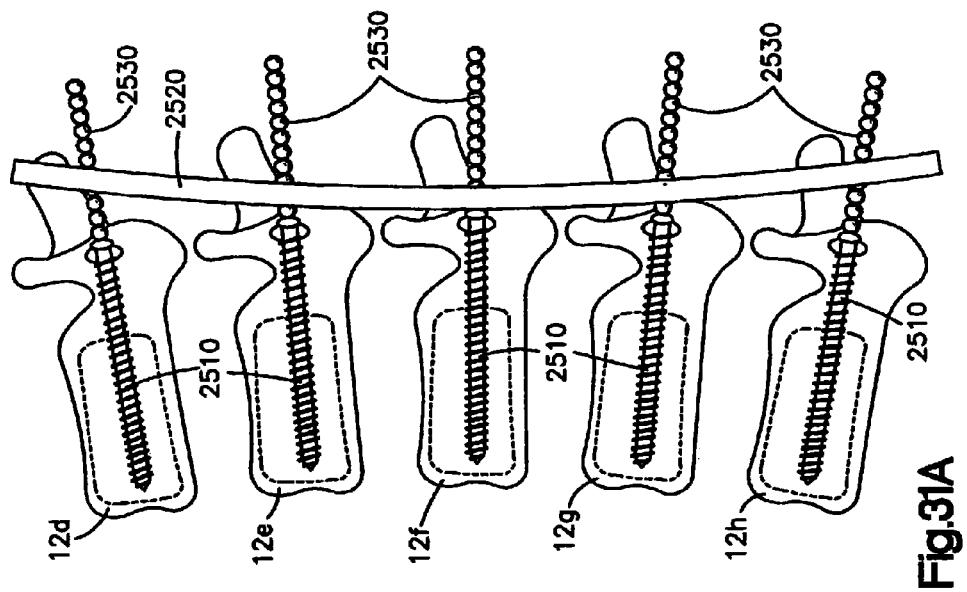

APPARATUS AND METHODS FOR VERTEBRAL AUGMENTATION USING LINKED EXPANDABLE BODIES

CROSS-REFERENCE TO RELATED APPLICATIONS

The present application is a continuation of U.S. patent application Ser. No. 12/704,421 filed Feb. 10, 2010, now U.S. patent No. 8,267,971 issued Sep. 18, 2012, which is a divisional of U.S. patent application Ser. No. 11/523,202 filed Sep. 18, 2006, which claims priority to U.S. Provisional Application Nos. 60/725,773 filed Oct. 12, 2005; 60/715,188 filed Sep. 8, 2005; 60/728,442 filed Oct. 19, 2005; 60/730,909 filed Oct. 27, 2005; 60/733,026 filed Nov. 3, 2005; 60/722,064 filed Sep. 28, 2005; 60/726,835 filed Oct. 13, 2005; 60/733,647 filed Nov. 4, 2005; 60/753,782 filed Dec. 23, 2005; 60/789,956 filed Apr. 5, 2006; and 60/748,377 filed Dec. 8, 2005.

FIELD OF THE INVENTION

The invention relates to surgical implants, and more particularly to minimally invasive apparatus and methods for augmenting and/or repositioning vertebrae and restoring of spinal lordosis.

BACKGROUND OF THE INVENTION

Vertebral compression fractures, as illustrated in FIG. 1, represent a generally common spinal injury and may result in prolonged disability. These fractures involve collapsing of one or more vertebral bodies 12 in the spine 10. Compression fractures of the spine usually occur in the lower vertebrae of the thoracic spine or the upper vertebra of the lumbar spine. They generally involve fracture of the anterior portion 18 of the affected vertebra 12 (as opposed to the posterior side 16). Spinal compression fractures can result in deformation of the normal alignment or curvature, e.g., lordosis, of vertebral bodies in the affected area of the spine. Spinal compression fractures and/or related spinal deformities can result, for example, from metastatic diseases of the spine, from trauma or can be associated with osteoporosis. Until recently, doctors were limited in how they could treat such compression fractures and related deformities. Pain medications, bed rest, bracing or invasive spinal surgery were the only options available.

More recently, minimally invasive surgical procedures for treating vertebral compression fractures have been developed. These procedures generally involve the use of a cannula or other access tool inserted into the posterior of the effected vertebral body through the pedicles. The most basic of these procedures is vertebroplasty, which literally means fixing the vertebral body, and may be done without first repositioning the bone.

Briefly, a cannula or special bone needle is passed slowly through the soft tissues of the back. Image guided x-ray, along with a small amount of x-ray dye, allows the position of the needle to be seen at all times. A small amount of polymethylmethacrylate (PMMA) or other orthopedic cement is pushed through the needle into the vertebral body. PMMA is a medical grade substance that has been used for many years in a variety of orthopedic procedures. Generally, the cement is mixed with an antibiotic to reduce the risk of infection, and a powder containing barium or tantalum, which allows it to be seen on the X-ray. Also, an iodine solution as an x-ray marker is often used in liquid form.

Vertebroplasty can be effective in the reduction or elimination of fracture pain, prevention of further collapse, and a return to mobility in patients. However, this procedure may not reposition the fractured bone and therefore may not address the problem of spinal deformity due to the fracture. It generally is not performed except in situations where the kyphosis between adjacent vertebral bodies in the effected area is less than 10 percent. Moreover, this procedure requires high-pressure cement injection using low-viscosity cement, and may lead to cement leaks in 30-80% of procedures, according to recent studies. In most cases, the cement leakage does no harm. In rare cases, however, polymethymethacrylate or other cement leaks into the spinal canal or the perivertebral venous system and causes pulmonary embolism, resulting in death of the patient.

More advanced treatments for vertebral compression fractures generally involve two phases: (1) reposition, or restoration of the original height of the vertebral body and consequent lordotic correction of the spinal curvature; and (2) augmentation, or addition of material to support or strengthen the fractured bone.

One such treatment, balloon kyphoplasty (Kyphon, Inc.), is illustrated in FIGS. 2A-D. A catheter having an expandable balloon tip is inserted through a cannula, sheath or other introducer into a central portion of a fractured vertebral body comprising relatively soft cancellous bone surrounded by fractured cortical bone (FIG. 2A). Kyphoplasty then achieves the reconstruction of the lordosis, or normal curvature, by inflating the balloon, which expands within the vertebral body restoring it to its original height (FIG. 2B). The balloon is removed, leaving a void within the vertebral body, and PMMA or other filler material is then injected through the cannula into the void (FIG. 2C) as described above with respect to vertebroplasty. The cannula is removed and the cement cures to augment, fill or fix the bone (FIG. 2D).

Disadvantages of this procedure include the high cost, the repositioning of the endplates of the vertebral body may be lost after the removal of the balloon catheter, and the possible perforation of the vertebral endplates during the procedure. As with vertebroplasty, perhaps the most feared, albeit remote, complications related to kyphoplasty are related to leakage of bone cement. For example, a neurologic deficit may occur through leakage of bone cement into the spinal canal. Such a cement leak may occur through the low resistance veins of the vertebral body or through a crack in the bone which has not been appreciated previously. Other complications include; additional adjacent level vertebral fractures, infection and cement embolization. Cement embolization occurs by a similar mechanism to a cement leak. The cement may be forced into the low resistance venous system and travel to the lungs or brain resulting in a pulmonary embolism or stroke. Additional details regarding balloon kyphoplasty may be found, for example, in U.S. Pat. Nos. 6,423,083, 6,248,110, and 6,235,043 to Riley et al., each of which is incorporated by reference herein in its entirety.

Another approach for treating vertebral compression fractures is the Optimesh system (Spineology, Inc., Stillwater, Minn.), which provides minimally invasive delivery of a cement or allograft or autograft bone using an expandable mesh graft balloon, or containment device, within the involved vertebral body. The balloon graft remains inside the vertebral body after its inflation, which prevents an intraoperative loss of reposition, such as can occur during a kyphoplasty procedure when the balloon is withdrawn. One drawback of this system, however, is that the mesh implant is not well integrated in the vertebral body. This can lead to relative motion between the implant and vertebral body, and consequently to a postoperative loss of reposition. Additional details regarding this procedure may be found, for example, in published U.S. Patent Publication Number 20040073308, which is incorporated by reference herein in its entirety.

Still another procedure used in the treatment of vertebral compression fractures is an inflatable polymer augmentation mass known as a SKy Bone Expander. This device can be expanded up to a pre-designed size and Cubic or Trapezoid configuration in a controlled manner. Like the Kyphon balloon, once optimal vertebra height and void are achieved, the SKy Bone Expander is removed and PMMA cement or other filler is injected into the void. This procedure therefore entails many of the same drawbacks and deficiencies described above with respect to kyphoplasty.

A wide variety of other instruments and methods are known for the repositioning of vertebral bodies to correct deformations in alignment or spinal curvature of the spine that may result from vertebral compression fractures or other disorders. Such instruments and methods can generally involve the use of bone screws, also referred to as bone anchors, that may be implanted in to vertebrae. Once implanted, the bone screws may be used to mount a suitable spinal fixation instrumentation, such as clamps, rods, or plates. Such spinal instrumentation can then be used, to achieve and maintain correction of the spinal deformity and to stabilize the repositioned vertebrae while the vertebrae fuse together. For example, referring to FIGS. 3A-D, various methods 30A, 30B, 30C and 30D can be used to apply forces (as shown by small arrows 32) to reposition fractured or displaced vertebrae, e.g., fractured vertebrae 35 and displaced vertebrae 36. Bone screws 38, rods 39 or other apparatus may be used to apply such forces 32 and to maintain proper alignment of the spine 34.

FIGS. 4-9 show examples of such various methods and apparatus that have been employed in the art to correct spinal deformities. For example, FIG. 4 shows an example of a typical pedicle screw and rod system 40 that may be used to reposition and stabilize vertebral bodies adjacent to a fractured vertebra. Referring to FIG. 5, an early effort at spinal reduction was a system 50 having threaded shafts to draw the vertebrae into proper alignment. Such an apparatus for use in straightening a spinal column by reducing displacement between adjacent vertebrae is disclosed, for example, in U.S. Pat. No. 4,611,581 to Steffee, the entirety of which is incorporated herein by reference.

In other systems, a separate reduction mechanism grasps the head of a bone screw implanted in a misaligned vertebral body. In such systems, the bone screw is generally braced against a rod or other longitudinal support element, and the screw head may be pulled to realign the vertebra toward the rod. For example, FIG. 6 shows a method 60 of pulling a bone screw or other anchoring element toward a rod, or longitudinal member (Universal Spine System, Synthes, West Chester, Pa.). FIG. 7 shows a method and apparatus 70 for reducing spinal deformity using a cable and a cable tensioning system as disclosed in U.S. Pat. No. 5,782,831 to Sherman. FIG. 8 shows a spinal fixation apparatus 80 comprising a screw with openings in the head section for accepting a tension-stable fastening device that may be looped around the longitudinal support element, as disclosed in U.S. Pat. No. 6,325,802 to Frigg. FIG. 9 shows a bone screw and rod apparatus 90 using strings for rod movement and stabilization as disclosed in U.S. Pat. No. 6,802,844 to Ferree. Each of the forgoing references is incorporated herein by reference in its entirety.

A drawback of all of the above-described apparatus and systems is that the rod or longitudinal element is fully pulled into a clamping mechanism of the screw or anchoring element, and firmly engaged. Such an arrangement can be cumbersome and difficult to maneuver into an appropriate position for moving the vertebrae in the desired direction, particularly considering the relatively large size of the components of most of the above-described systems.

Accordingly, there remains a need in the art to provide safe and effective apparatus and methods for minimally invasive osteopathic augmentation and to reposition vertebral bodies and restore lordosis of the spine.

SUMMARY OF THE INVENTION

The present invention provides an apparatus and methods for vertebral augmentation, preferably minimally invasive vertebral augmentation, and repositioning of vertebral bodies. In one embodiment, the present invention provides an implant and method for correction of vertebral fractures and other disorders of the spine. For example, a chain of linked bodies may be inserted into a vertebral body damaged by a vertebral compression fracture. As linked bodies are inserted into a vertebral body, they may fill a central portion of the vertebral body and may push against the inner sides of the endplates of the vertebral body, thereby providing structural support and tending to restore the vertebra to its original height. Additionally, the flexibility of the chain between the linked bodies may lead to a thorough integration of the implant into the bone. The chain may comprise one or more linked bodies that are configured to expand after insertion, e.g., to secure the chain within the vertebral body.

In other embodiments, a chain may be inserted into a bone such as a vertebral body, e.g., through the lumen of a cannula or other sheath, and such sheath may be removed after implantation within the bone. In such embodiments, the chain, or a portion thereof, can remain within vertebral body, for example, to continue augmenting the vertebra and maintain proper lordosis. In other embodiments, a PMMA or another bone cement or filler can be inserted into the augmented bone, e.g., through the sheath or cannula, prior to, together with or after the chain to further enhance fixation or repair of the damaged region. In other embodiments, the chain or portions thereof can be coated with bone cement or filler and inserted into the bone. The bone cement or filler coating can be inserted in an active or inactive state, and if inactive, the cement or filler can be later activated. In other embodiments, a portion of the chain implant may be left extending out of the vertebral body, such that the extended portion of the chain can function as a tensioning member to reposition or realign the vertebral body. In still other embodiments, some or all of the linked bodies of the chain can be removed after repositioning the bone, and PMMA or another filler can be injected into a void created by the chain.

The bodies of the chain may be comprised of any biocompatible material having desired characteristics, for example a biocompatible polymer, metal, ceramic, composite, a shape memory alloy, or any combination thereof. The bodies may be joined in series by flexible or semi-flexible links, which may be comprised of any biocompatible material having desired characteristics of flexibility, strength, and the like. For example, in some embodiments the links between bodies may be comprised of a thread or other relatively thin structure, for example a fiber or strand, of a biocompatible polymer, metal, ceramic, composite or other material having desired characteristics. In some embodiments, the bodies and/or links may be resorbable.

In some embodiments, a method of treating bone may include inserting inside a fractured bone, for example a vertebrae, a chain comprising one or more linked bodies. A bone cement or other filler may be added with or without the implanted device to aid in stabilizing the bone and securing the implant in place within the bone. For example, bone graphing material, such as bone chips or demineralized bone may be added within the bone, and about the chain a small plug of bone cement may be used to fix the chain in the vertebrae. In some embodiments, an additional implant, e.g., a pedicle screw or other implant, may be used in combination with the chain implant.

In some embodiments, a method of restoring lordosis and/or repositioning a vertebral body may comprise implanting one or more chains into a vertebral body through a pedicle, wherein a portion of the one or more chains may extend posteriorly from the pedicle, and applying a tensioning force to the extended portion of the chain to alter the position of the vertebra. The chain may comprise expandable bodies or other structures that increase in size or otherwise change configuration after insertion, e.g., to secure the chain within the vertebra. The chain may or may not be further stabilized by bone cement or bone morphogenic materials (bone graft materials) inserted into the vertebrae and may or may not be further supplemented with bone cement to plug the opening and hold the chain in position. The extended portion of the chain may be secured to a fixation member inside or outside the body of the patient to maintain the desired position of the vertebra.

In some embodiments, an apparatus for correcting curvature of a spine may comprise at least one longitudinal fixation member, one or more anchoring elements for securing to one or more vertebrae, and one or more tensioning members securing each anchoring element to the longitudinal fixation member. Methods of using such apparatus for restoring and maintaining a desired spinal curvature may comprise inserting one or more anchoring elements into one or more vertebrae; attaching a tensioning member to each anchoring element using a fastener or other attachment means; applying a tension force to the tensioning members to reposition the vertebrae and restore a desired curvature to spine; applying one or more longitudinal fixation members along the long axis of the spine; and fixing the tensioning members to the longitudinal fixation to maintain the desired spinal curvature.

In another embodiment, a kit comprises various combinations of assemblies and components according to the present invention. A kit may include, for example, a cannula and a chain of linked bodies according to the present invention. In other embodiments, a kit may include an implant, a tensioning member and/or a longitudinal fixation member. Such embodiments may also comprise a syringe or other apparatus for injecting a cement or other filler into a vertebral body.

BRIEF DESCRIPTION OF THE DRAWINGS

The invention and further developments of the invention are explained in even greater detail in the following exemplary drawings. The present invention can be better understood by reference to the following drawings, wherein like references numerals represent like elements. The drawings are merely exemplary to illustrate certain features that may be used singularly or in combination with other features and the present invention should not be limited to the embodiments shown.

FIG. 1 is an illustration of a spine having a vertical compression fracture in one vertebral body;

FIGS. 2A-D are illustrations of a prior art method for treating a vertical compression fracture;

FIG. 10 is an illustration of chain apparatus according to an embodiment of the present invention;

FIGS. 11A and B are side cross-sectional view illustrations of the apparatus of FIG. 10 in use to augment a vertebral body;

FIG. 12 is a top cross-sectional view illustration of a vertebral body containing an implant comprising linked bodies according to the present invention;

FIGS. 13A and B are side cross-sectional views illustrations of an augmented vertebral body according to an embodiment of the present invention;

FIG. 14 is a side cross-sectional view illustration of an apparatus and method for augmenting a vertebral body according to an embodiment of the present invention;

FIG. 15 is a side cross-sectional view illustration of another apparatus and method for augmenting a vertebral body according to an embodiment of the present invention;

FIGS. 19A and B are side cross-sectional view illustrations of a method and apparatus for repositioning vertebral bodies according to an embodiment of the present invention;

FIGS. 20A and B are side cross-sectional view illustrations of methods and apparatus for stabilizing repositioned vertebral bodies according to an embodiment of the present invention;

FIGS. 21 A and B are side cross-sectional view illustrations of another method and apparatus for repositioning vertebral bodies according to an embodiment of the present invention;

FIGS. 22A-D are side cross-sectional view illustrations of apparatus for repositioning, augmenting and stabilizing vertebral bodies according to an embodiment of the present invention;

FIGS. 23A-C are side cross-sectional view illustrations of a method of repositioning a damaged vertebral body according to an embodiment of the present invention;

FIGS. 24A and B are side cross-sectional view illustrations of a method of augmenting a vertebral body repositioned according to the method of FIGS. 23A-C;

FIGS. 25A and B are side view schematic illustrations of a method of reducing spinal curvature according to an embodiment of the present invention;

FIG. 26A is a top cross-sectional view illustration of an apparatus for reducing spinal curvature according to an embodiment of the present invention;

FIG. 26B is a posterior view of the apparatus of FIG. 26A;

FIGS. 30A and B are side cross-sectional view illustrations of a method and apparatus for repositioning a displaced vertebral body according to an embodiment of the present invention;

FIGS. 31A and B are side cross-sectional view illustrations of a method and apparatus for reducing spinal curvature according to an embodiment of the present invention;

DETAILED DESCRIPTION

A. Vertebral Augmentation Using Linked Bodies

Figure 3A:
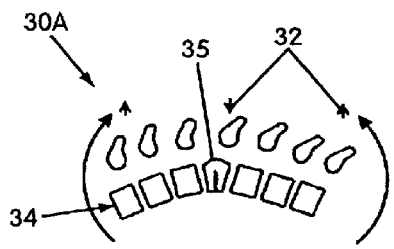
FIGS. 3A-D are schematic illustrations depicting various methods for applying forces to reposition fractured or displaced vertebrae.
Figure 3B:
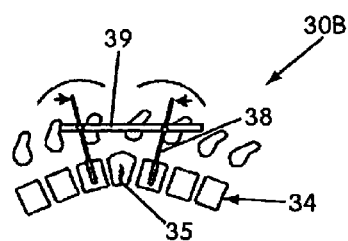
Figure 3C:
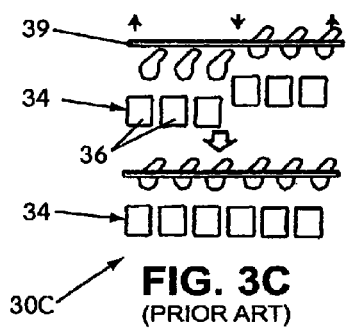
Figure 3D:
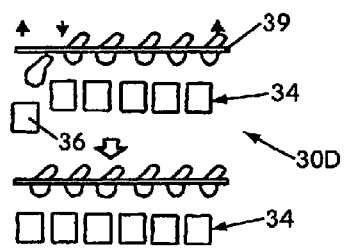
Figure 4:
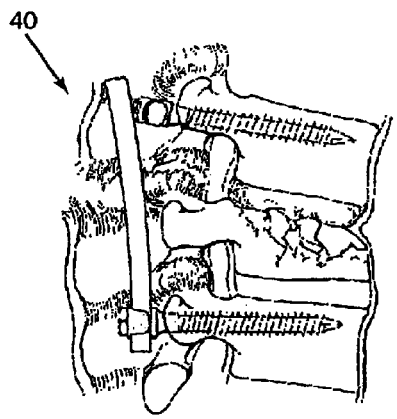
FIG. 4 is a an illustration of a prior art apparatus for repositioning vertebrae following a compression fracture.
Figure 5:
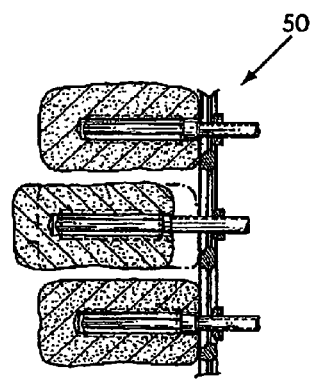
FIG. 5 is an illustration of a prior art apparatus for repositioning a displaced vertebra.
Figure 6:
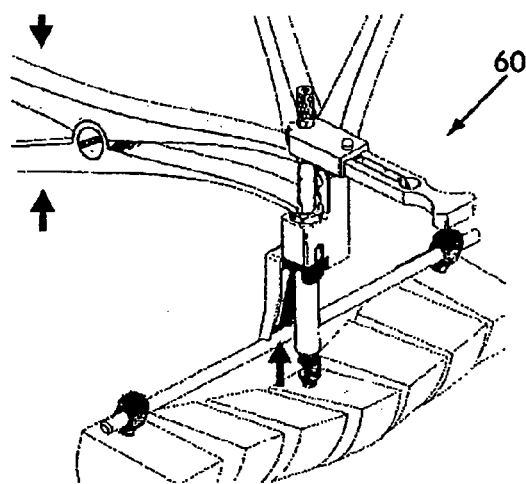
FIG. 6 is an illustration of another prior art system and method for repositioning displaced vertebrae.
Figure 7:
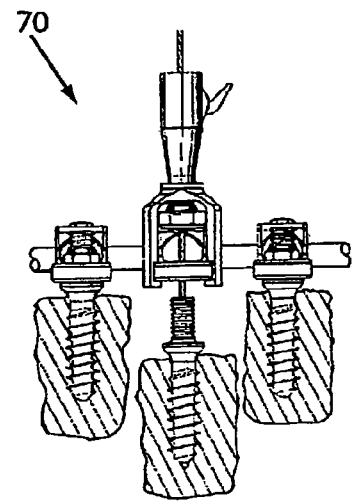
FIG. 7 is an illustration of another prior art apparatus for repositioning a displaced vertebra.
Figure 8:
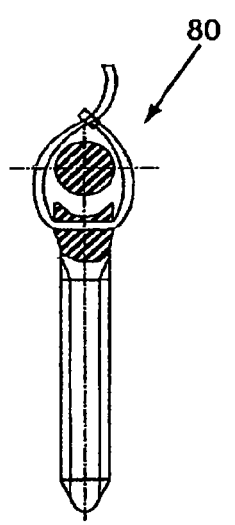
FIG. 8 is an illustration of a bone screw and rod apparatus known in the art.
Figure 9:
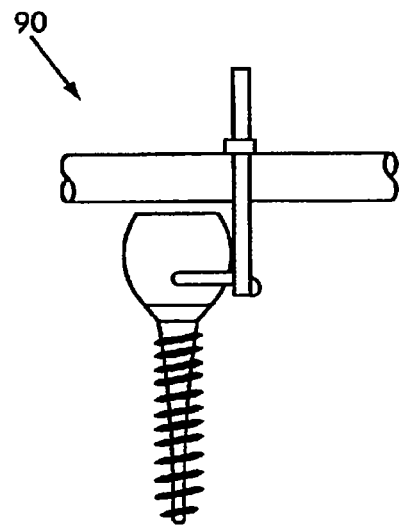
FIG. 9 is an illustration of another bone screw and rod apparatus known in the art.

Referring to FIG. 10, a chain 1000, comprises a plurality of linked bodies 100, or beads 100. The terms "bodies" and "beads" may be used interchangeably herein. Bodies 100 of chain 1000 may be comprised of any biocompatible material having desired characteristics, for example a biocompatible polymer, metal, ceramic, composite or any combination thereof. In some embodiments, the bodies 100 may be covered or coated, for example by a biodegradable polymer. The bodies 100 may also be covered or coated with an adhesive, antibiotics, osteoinductive material, and/or osteoconductive material. The adhesive may be activated by application of a energy source (e.g., an ultraviolet light, ultrasonic radiation, radio waves, heat, electric field, magnetic field) after the bodies have been inserted into the bone material. Bodies 100 may be rigid, elastic, flexible, soft, porous, non-porous, or may have any other desired characteristics. The bodies 100 may be filled with bone cement or other material. For example, the shell of the bodies may be a resorbable skin or membrane, while the inside of the bodies may comprise bone cement or other osteoinductive or osteoconductive material. Bodies 100 may be of uniform or non-uniform size, shape and materials, and may be linked in series, for example by one or more flexible or semi-flexible linking members 110, which can form joints of any desired length between bodies 100. A chain 1000 may have any desired number of linked bodies 100, and may have a first end 1001 and a second end 1002. In other embodiments, chain 1000 may be formed in a loop or other configuration having no ends, or may be configured to have multiple extensions and/or multiple ends, for example like branches of a tree.

In some embodiments, bodies 100 may be threaded upon a continuous or segmented thread, wire, fiber, strand or other elongated linking member 110. In other embodiments, each body 100 may be joined with adjacent bodies 100 by a segmented linking member. The one or more linking members 110 may be comprised of any biocompatible material having desired characteristics of flexibility, strength, and the like. For example, in some embodiments the linking members 110 between bodies 100 may be comprised of a wire or thread or other relatively thin structure of a biocompatible nylon, polymer, metal or any other material having desired characteristics. In some embodiments, bodies 100 and/or linking member 110 may be resorbable. The bodies 100 may be spaced along the linking member at uniform or nonuniform space increments, such that bodies 100 may or may not contact adjacent bodies.

Figure 33A:
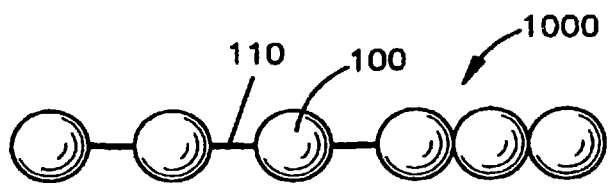
FIG. 33 are side view illustrations depicting different configurations of linked bodies and chains according to various embodiments of the present invention.
Figure 33B:
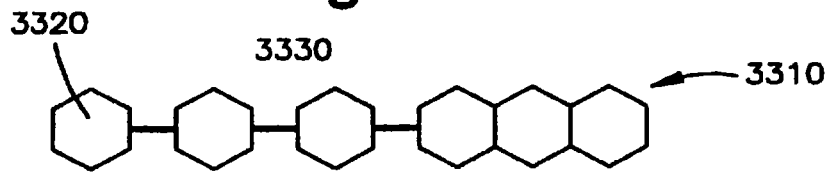
Figure 33C:
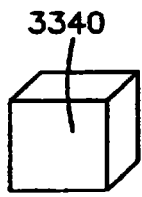
Figure 33D:
Figure 33E:
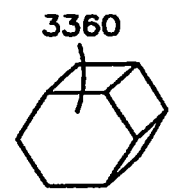
Figure 33F:
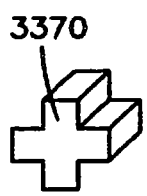
Figure 33G:
Figure 33H:
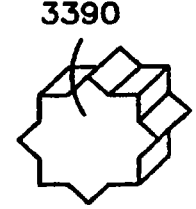

As shown in FIGS. 33A-C, linked bodies and chains described herein may have any desired geometry and/or configuration. For example, chain 1000 (FIG. 33A) may comprise substantially spherical linked bodies 100 joined by and/or threaded upon one or more linking members 110. In other embodiments chain 3310 (FIG. 33B) may have different configurations of linked bodies 3320 that may be joined by one or more linking members 3330. Linked bodies 100, 3320 may take any shape for example as shown by body shapes 3320, 3340, 3360, 3370 3380 or 3390 (FIG. 33C).

As shown in FIGS. 11A and 11B, a minimally invasive method 1100 of augmenting a damaged vertebral body 12, e.g., following a vertebral compression fracture, may comprise implanting one or more chains 1000 into an inner portion 1112 of a vertebral body 12 between endplates 1114 and 1116. A hole may be formed in the outer coritcal shell of vertebral body 12 by a trocar, drill or other instrument. Chain 1000 may then be implanted, for example, through a cannula 1102 or introducer inserted into vertebral body 12. Suitable procedures and materials for inserting a cannula through which chain 1000 may be introduced are known in the art, and may be similar to those described above for kyphoplasty and other procedures. For example, cannula 1102 may be introduced through the posterior portion 16 of vertebral body 12, e.g., through pedicle 14 (e.g., transpedicular approach) towards the anterior portion 18 of vertebral body 12. A chain may be inserted and may compact the cancellous and osteoporotic bone inside the collapsed vertebral body. Both a cannula and guide wire may be used together, or separately, to guide the bodies 100 of the chain 1000. Alternatively, neither the cannula or guide wire may be used to position the bodies 100, rather the chain 1000 may be inserted down a passageway formed in the bone by a physician.

A passageway may be formed into the interior of the vertebral body using a drill or other instrument. The chain 1000 may then be inserted in the passageway and may compact or compress the bone material inside the vertebral body. Alternatively, after the passageway is formed in the vertebral body, instruments such as, for example, currettes or balloon catheter may be used to compress and compact the bone inside the vertebral body to create a cavity. The cavity in the vertebral body 12 also may be formed by removing bone material as opposed to compacting the bone. For example, a reamer, currette or other apparatus could be used to remove bone material from the inside of the vertebral body. Also, curettes and other instruments may be used to move the endplates of the vertebrae to correct curvature of the spine.

As more linked bodies 100 of chain 1000 are inserted into vertebral body 12, they may fill central portion 1112 and can push against inner sides of endplates 1114 and 1116, thereby tending to restore vertebral body 12 to its original height and provide structural support to stabilize vertebral body 12. Additionally, the flexibility of one or more linking members 110 between linked bodies 100 may allow bending of the chain within space 1112, e.g., in a uniform pattern or in a non-uniform or tortuous configuration, to aid in ensuring a thorough integration of the implant 1000 within the bone 12. Bone cement or other filler material may be used in conjunction with the inserted bodies 100 to move the vertebrae endplates to correct curvature of the spine.

In other embodiments, chain 1000 may be inserted into a bone such as a vertebral body 12, e.g., through the lumen of a cannula 1102 or other sheath, and such sheath may be removed after implantation within the bone 12. In such embodiments, chain 1000, or a portion thereof, may remain in vertebral body 12, for example, to continue augmenting the vertebra and maintain proper lordosis. In other embodiments, PMMA or another bone cement or filler (for example bone chips) may be inserted into vertebral body 12, e.g., through shaft and/or a cannula 1102, along with linked bodies 100 to further enhance fixation or repair of the damaged region. In other embodiments, some or all linked bodies 100 of chain 1000 may be removed after repositioning the bone, and PMMA or another bone cement or filler may be injected into a void created by chain 1000. Alternatively, a bone growth promoting filler may be inserted into vertebral body 12 and a plug of base cement utilized to hold the linked bodies and filler material in the vertebrae.

FIG. 12 is a top cross-sectional view illustration of a vertebral body 12 having one or more chains 1000 implanted within portion 1112 of vertebral body 12. The one or more chains 1000 may comprise a plurality of bodies 100, which may be joined in series by one or more linking members 110 as described above. One or more cannulae 1102, each for example having a lumen 1104 of sufficient size for passing linked bodies 100, can be used to implant chain 1000 into vertebral body. The one or more cannulae 1102 may be inserted into vertebral body 12 through pedicles 14. In some embodiments, the cannulae may be left within vertebral body, and remain extending from pedicles, for example held in place by threads (not shown).

In some embodiments, chains 1000 may be implanted completely within vertebral body 12 as shown in FIG. 13A, and the cannulae or other introducer may be removed. As shown in FIG. 13B, other implants or apparatus, for example bone screw 1300, may be inserted into vertebral body 12 in conjunction with chain implant 1000. Such additional implants 1300 may be used to further augment vertebral body 12, and/or may be used as an anchoring element for repositioning the vertebral body 12 as shown and described in more detail below, for example with respect to FIGS. 27-32. Screw 1300 may be hollow or solid, and may be comprised of a stainless steel, a metal alloy, a ceramic, polymer, composite or any other desired material. In some embodiments, screw 1300 may be hollow, e.g., including a lumen such as lumen 1104 of cannula 1102, and used as an introducer to create a passage for passing chain 1000 into vertebral body 12. A bone cement or other material (such as, for example, an adhesive, a polymer, bone chips, or demineralized bone) may be injected into vertebral body 12 before, during or after insertion of implants 1000 and/or 1300 to further secure the implants and/or augment vertebral body 12.

Referring to FIGS. 14 and 15, chain 1000 may be inserted through cannula 1102 into central portion 1112 of vertebral body 12 using a number of different apparatus, e.g., 1400 and 1500. In one embodiment, a plunger, pusher or other displacement member 1400 inserted within cannula 1102 may be used to displace or push bodies 100 of chain 1000 through cannula 1102 and into vertebral body 12. Displacement member 1400 may be driven, for example, by pressure, e.g., from a syringe, rod, or other apparatus that forces displacement member 1400 into cannula 1102 and towards vertebral body 12. In another embodiment, a sprocket 1500 or apparatus that may be wheel-like and have teeth, gears or other extensions 1502 may be configured to engaging bodies 100 of chain 1000. As sprocket 1500 rotates about a central axis 1504, for example in a direction shown by arrow 1506, teeth 1502 may engage bodies 100 and force chain 1000 through cannula 1102 and into portion 1112 of vertebral body 12. In other embodiments, sprocket 1500 may be rotated in an opposite direction to remove some or all of chain 1000, for example after restoring a height of vertebral body 12.

Figure 16:
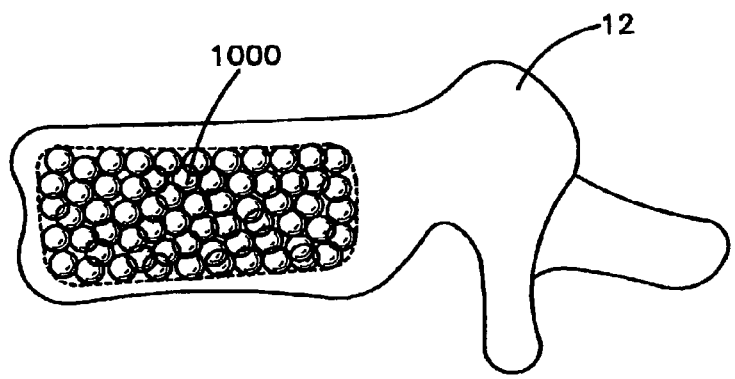
FIG. 16 is a side cross-sectional view illustration of an augmented vertebral body according to an embodiment of the present invention.
Figure 17:
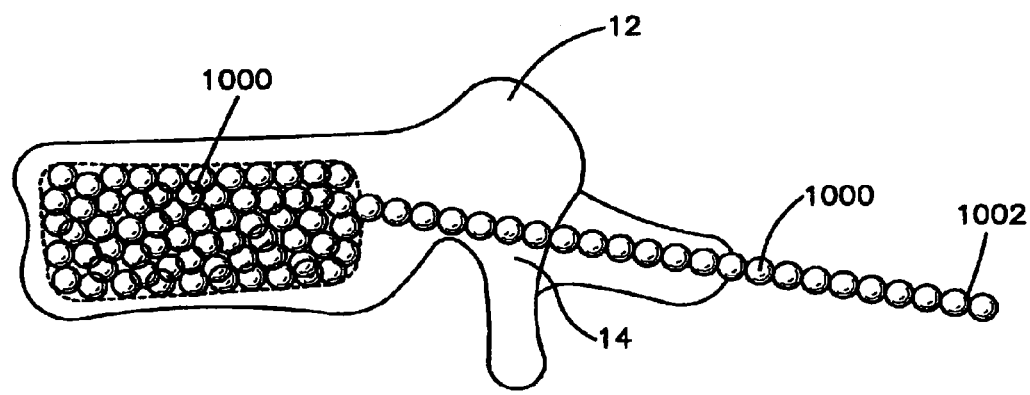
FIG. 17 is a side cross-sectional view illustration of an augmented vertebral body including an extended chain of linked bodies according to another embodiment of the present invention.

As shown in FIG. 16, one or more chains 1000 may be implanted completely within a vertebral body 12. In other embodiments, a portion of chain 1000 may be left extending from vertebral body 12. For example, as shown in FIG. 17, one or more ends 1002 may extend through one or more pedicles 14 of vertebral body. As shown and described in other embodiments below, end 1002 may be used as a tensioning member to reposition vertebral body 12, for example to restore a desired curvature to a spine.

Figure 18A:
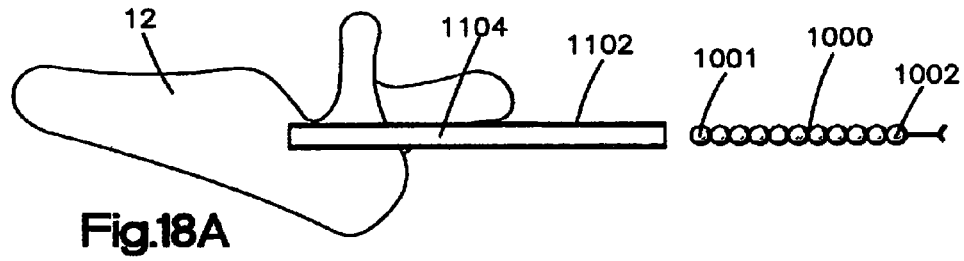
FIGS. 18A-E are side cross-sectional view illustrations of a method of augmenting a vertebral body using a chain of linked bodies according to an embodiment of the present invention.
Figure 18B:
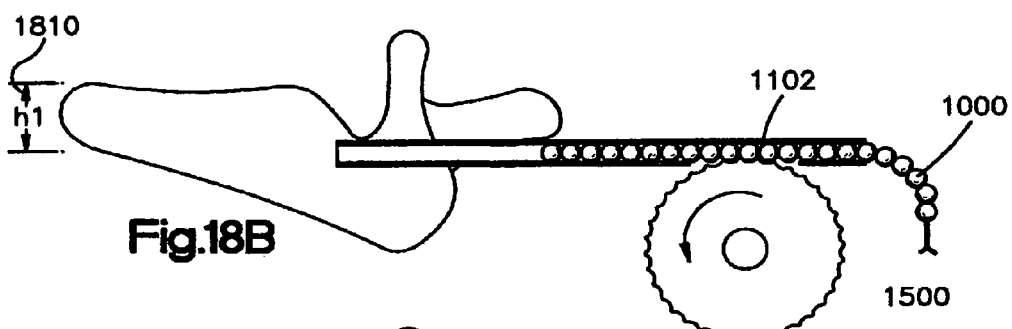
Figure 18C:
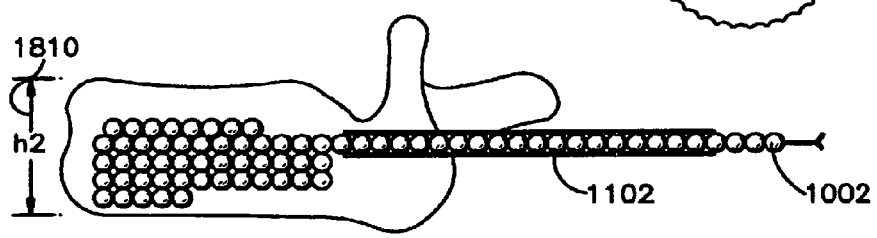
Figure 18D:
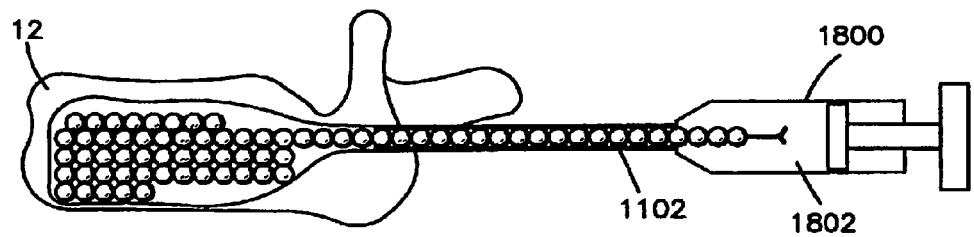

FIGS. 18A-E are side cross-sectional view illustrations of a method of augmenting a vertebral body 12 using a chain 1000 of linked bodies according to one embodiment. As shown in FIG. 18A, cannula 1102 may be inserted into vertebral body 12, for example in a posterior transpedicular approach as described above, and an end 1001 of chain 1000 may be inserted into lumen 1104 of cannula 1102. As shown in FIG. 18B, a sprocket device 1500 or other insertion apparatus may then be used to engage and implant chain 1000 into vertebral body 12. As linked bodies of chain 1000 are implanted, height 1810 of vertebral body is increased, for example from h1 to h2. As shown in FIG. 18C, a desired length of chain 1000 at end 1002 may be left extended from cannula 1102. As shown in FIG. 18D, a syringe 1800 or other apparatus may be attached to cannula 1102 and used to inject a filler material 1802, such as, for example, a bone growth promoting substance or bone cement into vertebral body. During or after injection of the filler material, cannula 1102 may be removed from vertebral body 12. After the area occupied by the linked bodies has been filled with the filler material 1802, and the cannula 1102 has been removed from within the vertebrae so that it is positioned against the outside of the vertebrae, or just adjacent (and preferably just inside the vertebrae) a bone cement may be inserted to form a plug 1804 to retain the linked bodies and/or filler material 1802 in place in the vertebrae.

Figure 18E:
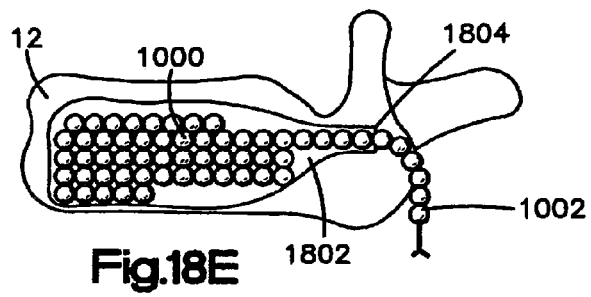

As shown in FIG. 18E, a desired length of amount of chain 1000 can be left within vertebral body 12, along with filler material 1802, to augment vertebral body 12. A desired length of chain at end 1002 may be left extended from vertebral body 12 as shown. In some embodiments, the portion of chain 1000 extending from vertebral body may be detached from the portion of the chain within vertebral body 12, for example after using end 1002 as a tensioning member to reposition the vertebral body 12 as described in more detail below.

In some embodiments, a cement or other substance (such as, for example, a polymer) may be injected into a bone, e.g., vertebra 12 along with chain 1000 of linked beads or bodies 100, simultaneously or otherwise. For example, a double lumen catheter (not shown) can be used, wherein the cement is injected through one lumen and the beads or bodies through another lumen. The cement and beads in the double lumen catheter could exit the catheter at different or the same places, and materials from the two lumens could enter vertebrae without mixing or contacting until they are injected into the vertebral space. Alternatively, the double lumen catheter could have one or more exit ports distributed throughout its length, or at least at one location, such that all or some of the cement contacts and is distributed over the beads before injection into the vertebrae or other bone. The catheter could remain a double lumen catheter or converge into a single lumen. Also, the beads and cement can be injected simultaneously through the same lumen. Alternatively, the beads can be injected through the lumen of the catheter and subsequently the cement or other material can be injected through the lumen in the catheter after the beads have been placed in the vertebrae, but while the beads still extend out of the vertebrae opening and while beads are still present in the catheter. Alternatively, or in addition, the cement or other material can be injected or placed in vertebrae before the beads.

In some embodiments, flexible chain 1000 may be coated with an adhesive or a polymer coating, such that chain 1000 may inserted into vertebral body 12 in a flexible state and may become hardened, tangled and/or convoluted during or after insertion. After insertion, bodies 100 may become attached together by the adhesive so that the flexible chain becomes a mass that may be locked into the vertebral body, or otherwise secured such that chain 1000 may not be easily removed through the insertion opening.

In other embodiments, linked bodies 100 may be coated with an adhesive and the chain may be inserted, with or without becoming tangled or convoluted, into a vertebral body 12. During or after insertion of some or all linking bodies 100 of a chain 1000, a portion of chain 1000 may be exposed to an energy source (e.g., an ultraviolet light, ultrasonic radiation, radio waves, heat, electric field, magnetic field), for example to activate the adhesive, such that the exposed portion of chain 1000 becomes joined to form a mass, or becomes rigid, or both, thereby further augmenting the vertebral body 12 and/or preventing removal of chain 1000 through the insertion opening.

B. Vertebral Repositioning and Restoration of Lordosis Using Linked Bodies

FIGS. 19A and B are side cross-sectional view illustrations of a portion of a spine comprising vertebrae 12A, 12B and 12C, where vertebral body 12*b* has been damaged, for example due to a vertebral compression fracture resulting in a deformation of the normal curvature of the spine. In a method of repositioning vertebrae 12*a*, 12*b* and/or 12*c* to restore the normal curvature, chains 1000 comprising linked bodies 100 may be implanted into vertebral bodies 12*a* and 12*c*, which are adjacent to fractured vertebral body 12*b*. As described above with respect to FIGS. 18A-E, one or more chains 1000 may be implanted, with a portion of chains 1000 at one end 1002 extending through one or more pedicles of vertebrae 12*a* and 12*c*. In some embodiments, a bone cement or other filler may be used to further augment vertebrae 12*a* and 12*c*, and/or fix chains 1000 in place. A force can be applied as depicted by arrow 1900 to reposition or tilt vertebra 12*a* upward and restore the height 1910 of vertebral body 12*b* from a height of h1 as shown in FIG. 19A to its normal height of h2 as shown in FIG. 19B. Such repositioning of vertebrae 12*a* and 12*b* also may tend to restore the normal lordosis, or curvature, of the spine.

After repositioning the vertebral bodies 12*a* and 12*b* as shown in FIGS. 19A and 19B, vertebrae 12*a*, 12*b* and/or 12*c* may be fixed in a desired position, for example by attaching a longitudinal fixation member 2000 to ends 1002 of chains 1000 (FIGS. 20A and 20B). Chains 1000 may be attached to fixation member 2000 using, for example, fasteners 2012 and 2014 or other devices attached to or integral within fixation member 2000. In some embodiments, fixation member 2000 may be positioned outside the patient's body, e.g., against the skin 2010 of the patient. In other embodiments, the longitudinal fixation member may be positioned within the body of the patient and anchored against the vertebrae, 12*a*, 12*b* and/or 12*c*.

FIGS. 21 A and B are side cross-sectional view illustrations of another method and apparatus for repositioning vertebral bodies according to an embodiment. As described above with respect to FIGS. 20A and B, one or more chains 1000 may be inserted into vertebral bodies 12*a* and 12*c*, which may be adjacent to a damaged vertebral body 12*b*. Chains 1000 may be implanted with or without a bone cement or other filler 1802, for example through a hole 2120 in pedicles of vertebral bodies 12*a* and 12*c*. Ends 1002 may preferably extend from the posterior of vertebral bodies 12*a* and 12*c* and attach to a fixation member 2100, which may be a rod having a diameter 2102 as shown by the cross sectional view above member 2100. In some embodiments, chains 1000 may pass through holes (not shown) in rod 2100 and/or through clamps or fasteners (not shown) associated with rod 2100. Rod 2100 may comprise a biocompatible metal, a metal alloy, a polymer, ceramic, a carbon composite, or any other material having desired properties, for example, of strength, stiffness, and elasticity.

As shown in FIG. 21B, tension forces 2112 and 2114 may be applied to pull ends 1002 of chain 1000, and an opposing force 2110 may be applied to fixation member 2100 approximately between chains 1000. Such forces 2112, 2114 and 2110 may pull chains 1000 past or through rod 2100 and reposition vertebrae 12*a*, 12*b* and 12*c*, thereby restoring the height of vertebra 12*b*. After tensioning ends 1002 of chains and restoring vertebrae 12*a*, 12*b*, and 12*c* to a desired position, chains 1000 may be fixed to fixation rod 2100 to maintain the position. In other embodiments, chains 1000 may be attached to rod 2100 before applying forces 2110, 2112 and 2114, and rod 2100 may bend with application of such force and be secured in a desired position with another fixation member (not shown).

Figure 22D:
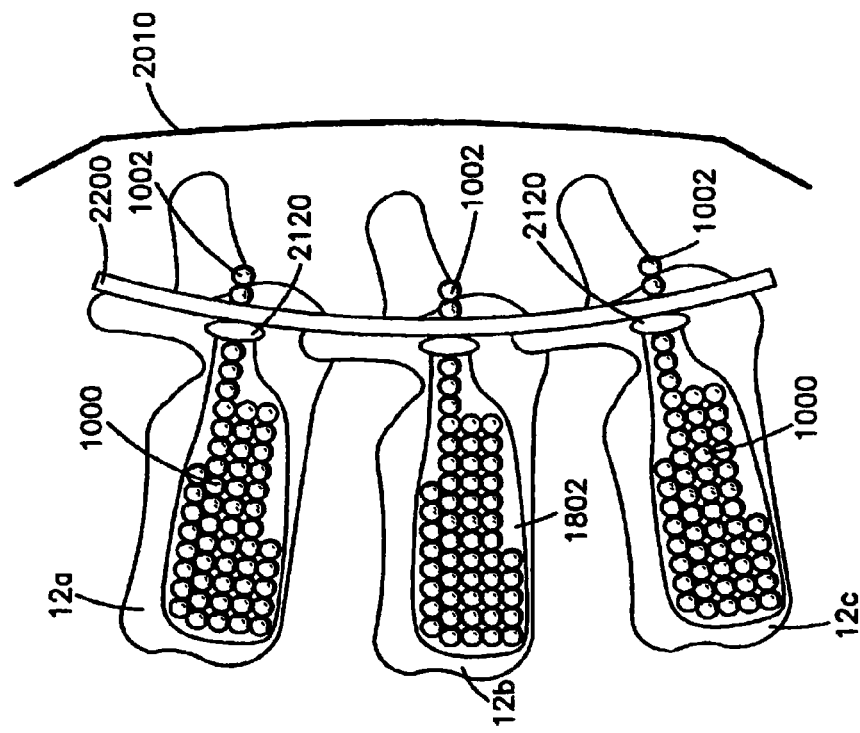
Figure 22C:
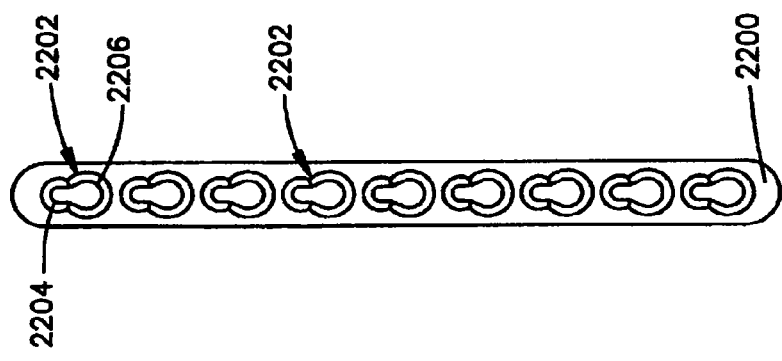

Referring now to FIGS. 22A-D, another method and apparatus for repositioning, augmenting and/or stabilizing vertebral bodies may comprise using an elongated fixation member 2200 having slotted holes 2202 or other features to releasably and adjustably secure chains 1000. For example, as shown in FIGS. 22B and 22C, slotted holes 2202 may include a passage 2206 having a diameter larger than a diameter of the linked bodies 100 of chain 1000, such that chain 1000 and bodies 100 may pass through passage 2206 adjacent to and in communication with a notch or slot 2206 which is larger than linking member 110 but smaller than linked bodies 100. Chain 1000 may be secured to fixation member 2200 by translating a body 100 of chain in the direction of the long axis A of member 2200 such that body 100 may be retained by notch 2204 adjacent to passage 2206. Fixation member 2200 may include a plurality of such holes 2202. Like rod 2100, fixation member 2200 may comprise a biocompatible metal, a polymer, a ceramic, a composite, or any other material having desired properties, for example, of strength, stiffness, and elasticity.

In use, fixation member 2200 and chains 1000 may be used in a similar manner as described above with respect to FIGS. 20A and B and/or FIGS. 21A and B to augment and/or reposition damaged or deformed vertebrae. Briefly, fixation chains 1000 may be implanted into vertebral bodies 12a and 12c with or without bone cement or other filler 1802 as described above, and tensioning forces may be applied to ends 1002 of chains 1000 to improve spinal curvature and/or increase the height of a damaged vertebra 12b. Once chains 1000 are pulled through passages 2206 holes 2202 of fixation member 2200 to produce a desired orientation of vertebrae, chains 1000 may be locked into slots 2204 and secured in place to fixation member 2200.

As shown in FIG. 22D, damaged vertebral body 12b may also be augmented with a chain implant 1000 and/or filler 1802, for example before or after repositioning the vertebrae 12a, 12b and 12c. In some embodiments, fixation member 2200 and/or end 1002 of chain may be positioned against a posterior aspect of vertebrae 12a, 12b and/or 12c, and/or implanted underneath the skin 2010 of the patient. In other embodiments, fixation member 2200 and/or a portion of chain 1000 at end 1002 may be removed from the patient after vertebrae are repositioned and augmented with chains 1000 and/or bone cement or other filler 1802. In some embodiments, a portion of end 1002 of chain 1000 may be removed after securing chain 1000 to fixation member 2200.

In other embodiments, as shown in FIGS. 23A-C, vertebral bodies 12a, 12b and 12c may be repositioned and/or augmented with fixation member 2200 remaining substantially outside of the body of the patient, e.g., outside skin 2010. Again using an example of a vertebral body 12b damaged due to a compression fracture, adjacent vertebral bodies 12a and 12c may be augmented with chains 1000 and/or filler 1802 as described above. Ends 1002 of chains may extend posteriorly from vertebrae 12a and 12c and to the outside of the patient's body. An anchoring element 2300 may be inserted and/or secured into a posterior aspect of vertebra 12b, for example through a pedicle. In some embodiments, anchoring element 2300 may be a screw or bolt, for example a monoaxial or polyaxial top loading pedicle screw, which may or may not have threads for securing to vertebra 12b, and may or may not include a lumen 2304. In some embodiments, a needle 2306 or other elongated member may be passed through lumen 2304 of anchoring element 2300, for example to secure vertebra 12b and/or provide a passage for injecting a bone filler or other material. Anchoring element 2300 may also include a flange, nut, fastener or other stop 2302 to secure against elongated fixation member 2200.

To reposition the alignment of vertebrae 12a, 12b and 12c, and to increase the height of vertebra 12b, tensioning forces 2312 and 2314 may be applied to chains 1000, and an opposing force 2310 may be applied to anchoring element as shown in FIG. 23C. When vertebrae 12a, 12b, and 12c are positioned as desired, chains 1000 may be locked into slots 2204 of holes 2202 of fixation member 2200.

In some embodiments, as shown in FIGS. 24A and 24B, after repositioning vertebrae 12a, 12b, and 12c, for example using apparatus and methods of FIGS. 23A-C, vertebra 12b may be further augmented using a chain 1000 and/or bone cement or other filler 1802 inserted into vertebral body 12b, for example through anchoring element 2300. After vertebrae 12a, 12b and 12c are positioned and augmented as desired, fixation member 2200 may be removed and/or a portion of chains 1000 extending from vertebrae 12a, 12b and/or 12c may be removed as shown in FIG. 24B.

Turning now to FIG. 25, other embodiments of apparatus and methods may be used to correct deformations of spinal curvature and/or to reposition displaced vertebrae. In general, an apparatus 2500 for correcting curvature of a spine 2502 may comprise at least one longitudinal fixation member 2520, one or more anchoring elements 2510 for securing to one or more vertebrae 12, and one or more tensioning members 2530 securing each anchoring element to the longitudinal fixation member 2520. In some embodiments, longitudinal fixation member 2520 may have similar features and/or serve similar functions to fixation member 2200; anchoring element 2510 may have similar features and/or serve similar functions as chain implant 1000 within a vertebral body; and tensioning member 2530 may have similar features and/or serve similar functions as end 1002 of chain that secures to fixation member as described in embodiments above.

Exemplary methods of using the apparatus 2500 of FIG. 25 to restore and maintain a desired spinal curvature may comprise inserting one or more anchoring elements 2510 into one or more vertebrae 12 and attaching a tensioning member 2530 to each anchoring element using a fastener or other attachment means (not shown). With tensioning member 2530 attached to anchoring element 2510, a tension force may be applied to pull on the tensioning members and reposition the vertebrae 12 to restore a desired curvature to spine 2500. After repositioning the vertebrae 12 and/or restoring a desired curvature to spine 2500, one or more longitudinal fixation members 2520 may be applied along the long axis of spine 2500, and tensioning members 2530 may be secured to the longitudinal fixation members to maintain the spine 2500 in the desired position.

Referring to FIGS. 26A and 26B, an embodiment of apparatus 2500 for adjusting spinal curvature according to an embodiment may comprise anchoring element 2510 inserted through pedicles 14 of vertebrae 12. Anchoring element 2510 may comprise a bone screw as shown, and/or another implant or device capable of securing to vertebral body 12 and imparting forces thereto. A tensioning member 2530 may secure to each anchoring element, e.g., near an end 2610 of anchoring element 2510 as shown in FIG. 26A. After applying forces to tensioning members 2530 to reposition vertebrae 12 as desired, tensioning members 2530 may be applied to one or more longitudinal fixation members 2520. For example, two longitudinal fixation members may be employed, e.g., one for securing to anchors implanted into the right pedicles 14R of vertebrae 12 and one for securing to anchors 2510 implanted into the left pedicles 14L of vertebrae 12.

Figure 27:
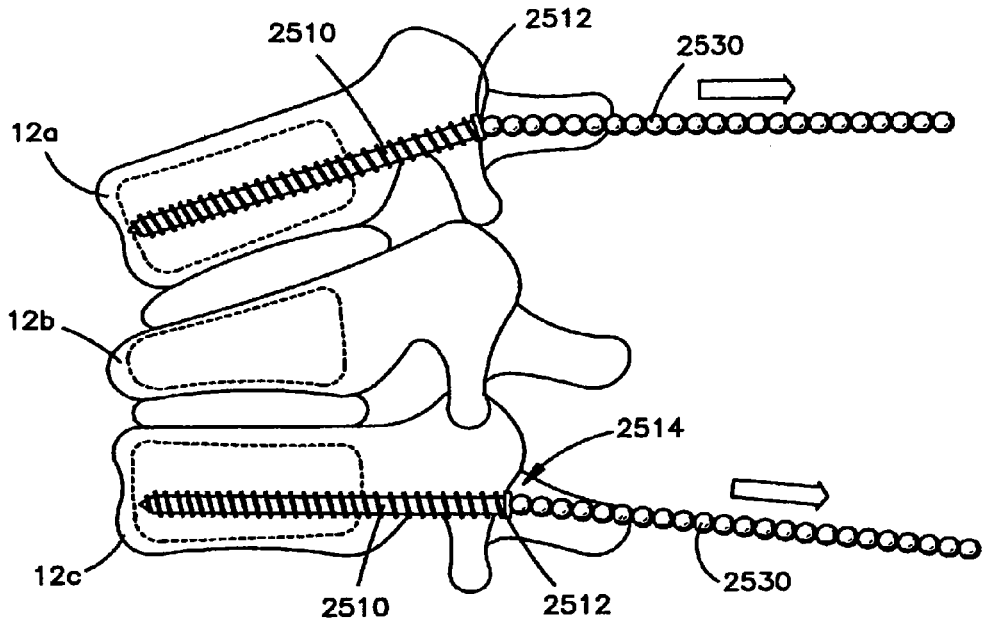
FIG. 27 is a side cross-sectional view illustration of a method and apparatus for repositioning a fractured vertebral body according to an embodiment of the present invention.
Figure 28:
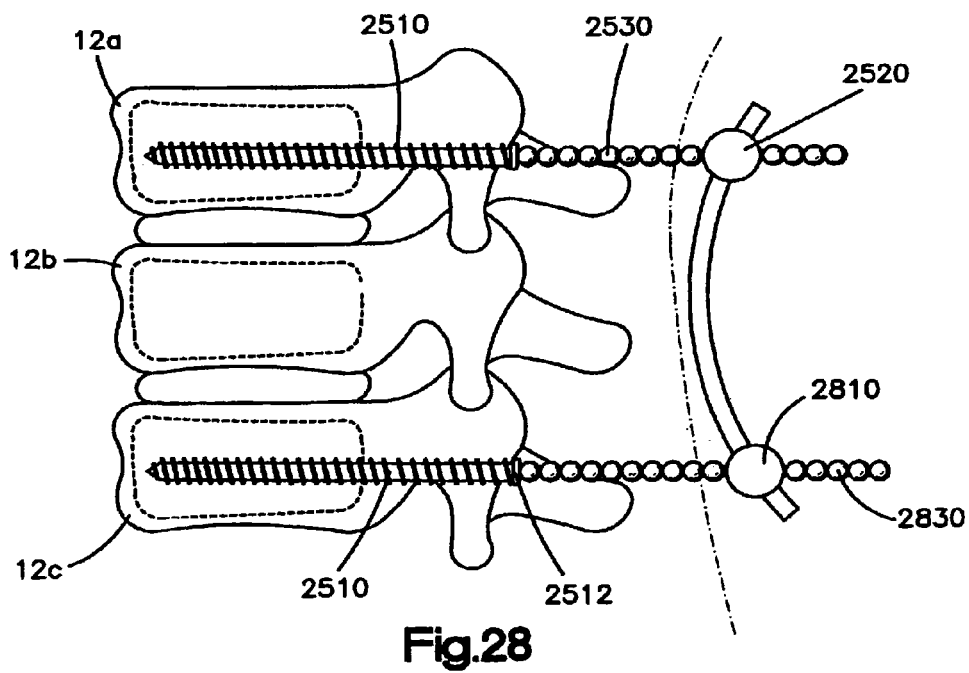
FIG. 28 is a side cross-sectional view illustration of a method and apparatus for fixing vertebral bodies repositioned according to the method of FIG. 27.
Figure 29:
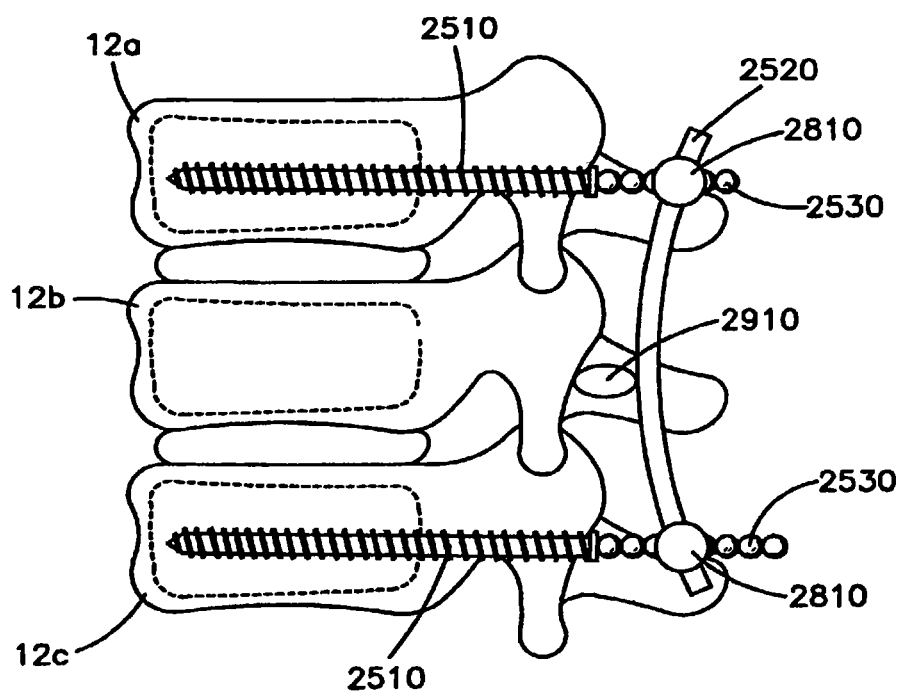
FIG. 29 is a side cross-sectional view illustration of another method and apparatus for fixing vertebral bodies repositioned according to the method of FIG. 27.

Referring now to FIGS. 27-29, different embodiments of apparatus 2500 may include similar features as, for example, the apparatus and methods described with respect to FIGS. 19A-24B for augmenting and repositioning vertebrae. For example, tensioning members 2530 may comprise one or more chains having similar features and/or functions as chain 1000. Anchoring element 2510 may be a bone screw, a bolt, an implanted chain, or another implant or device secured to vertebral body 12. Tensioning member 2530 may be fixed or otherwise secured to an end of anchor element 2510, for example, to a head 2512 of bolt 2510 by a fastener 2514, e.g. a slot feature or other fastener or fastening means for securing element 2530 to bolt 2510. By imparting a tensioning force to elements 2530, vertebrae 12a, 12b and/or 12c may be repositioned as described above.

Referring to FIG. 28, after vertebral bodies 12a, 12b and/or 12c are repositioned to provide a desired orientation or curvature of the spine, tensioning member 2530 may be secured to an elongated fixation member 2520, e.g. using fasteners 2810. In other embodiments, fixation member 2520 may include slotted holes 2202 or similar features as fixation member 2200 described above. In some embodiments, fixation member 2520 may be secured outside of the body of the patient as shown in FIG. 28. In other embodiments, fixation member 2520 may be secured within the patient and closer to vertebrae 12 as shown in FIG. 29. In such embodiments, for example, a spacer element 2910 or other anchor may be used to provide an interface between fixation member 2520 and vertebral body 12b.

Referring to FIGS. 30A and 30B, a method and apparatus for repositioning a displaced vertebral body according to an embodiment may comprise attaching an anchoring element 2510, e.g. a bone screw as shown, to each vertebrae 12a, 12b and 12c. Tensioning members 2530, which may comprise chains of linked bodies as described previously herein, may be used to transmit forces 3010, 3012 and 3014 to vertebrae 12a, 12b and 12c. In some embodiments force 3010 may be greater than forces 3012 and 3014, for example to reposition displaced vertebral body 12b into proper alignment and restore a normal curvature to the spine. Once vertebrae 12a, 12b and 12c are positioned in a desired alignment, one or more tensioning members 2630 may be secured to longitudinal fixation member 2520.

As shown in FIGS. 31A and 31B, any number of anchoring elements 2510 and tensioning members 2530 may be utilized to provide a desired vertebral alignment. For example, a spine having a deformed curvature as shown in FIG. 31A by the alignment vertebrae 12d, 12e, 12f, 12g and 12h, may be repositioned using one or more anchoring elements 2510 and tensioning member 2530 secured through the pedicles of each vertebrae 12d, 12e, 12f, 12g, and 12h as desired. Forces such as tension forces 3110 3112, 3114 and 3116 may be applied to one or more of the tensioning members 2530 to produce a desired curvature. The tensioning members 2530 may be secured to one or more elongated fixation members 2520 to maintain the forces 3110, 3112, 3114 and 3116 and fix the alignment as desired.

Figure 32A:
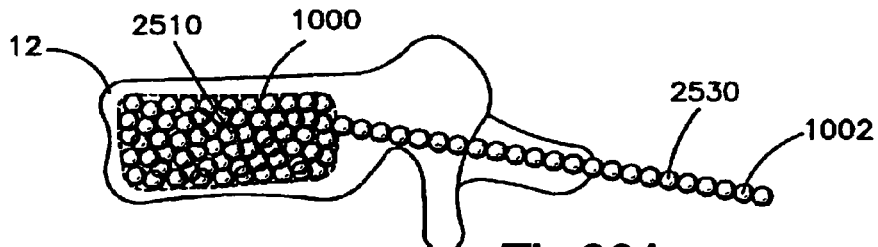
FIGS. 32A-E are side cross-sectional view illustrations of apparatus for treating spinal deformities according to various embodiments of the present invention.

Referring to FIGS. 32A-E, various different structures may be used to perform the functions of the anchoring element and/or tensioning member. For example, as shown in FIG. 32A, chain 1000, or another flexible or non-rigid structure, can serve as both an anchoring member 2510 and a tensioning member 2530. For example, chain 1000 of linked bodies 100 may be implanted as described elsewhere herein within a vertebral body 12, and may or may not be supplemented with an adhesive, a cement or other substance or structure, to function as an anchoring member 2510. End 1002 of chain 1000 may extend from the vertebra 12 to serve as the tensioning member 2530, for example to impart forces to reposition the vertebra 12.

Figure 32B:
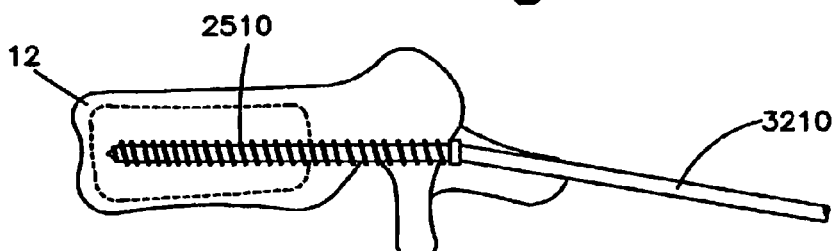
Figure 32C:
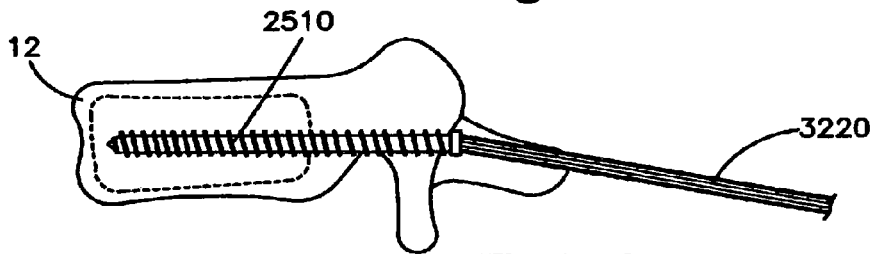
Figure 32D:
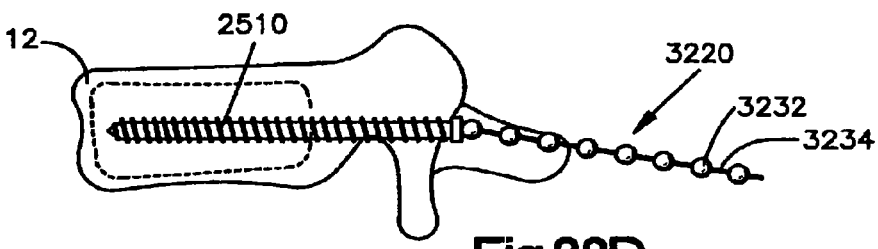
Figure 32E:
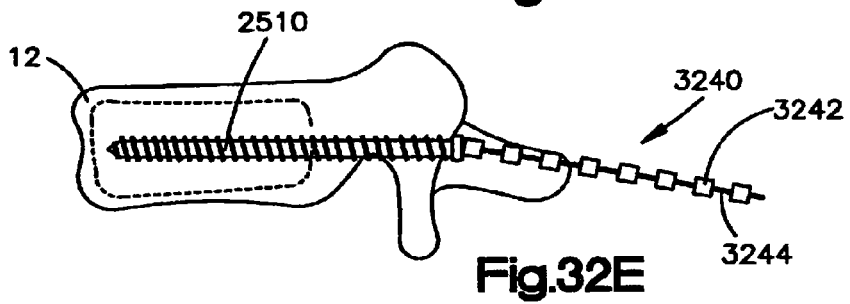

In other embodiments, a bone screw 2510 or other anchoring element may be attached to: a wire 3210, for example as shown in FIG. 32B; a single or multi-braided cable 3220, as shown in FIG. 32C; a chain 3230 having substantially spherical bodies 3232 linked by linking members 3234 of any length; and/or a chain 3240 having non-spherical bodies 3242 linked by linking members 3244. A screw having a lumen may be inserted in the vertebrae and the chain may be inserted through the lumen and into the vertebral body. A filler may be inserted down the lumen of the pedicle screw to augment and link the chain to the screw.

C. Expandable Linked Bodies

Figure 34A:
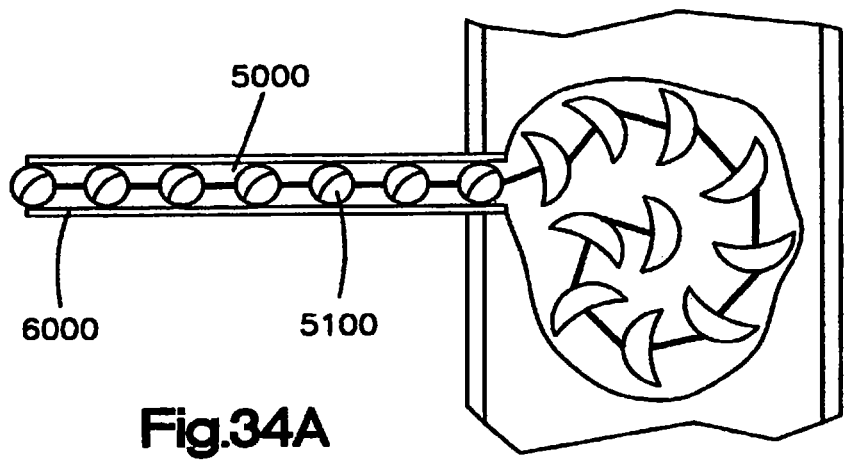
FIGS. 34 A-C are side view illustrations of an implant comprising expandable bodies during insertion into a bone.
Figure 34B:
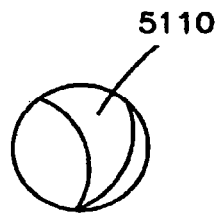
Figure 34C:
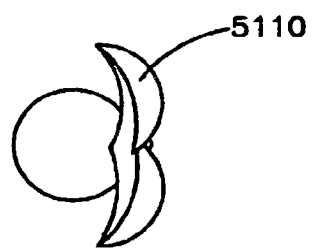

As shown in FIGS. 34-36, a chain or other implant 5000 may comprise one or more expandable bodies 5100 to fix the implant within a vertebral body or other bone after insertion. Such expandable bodies 5100 may be used instead of or in addition to filler material, such as, for example, cement, adhesive, glue, bone chips, demineralized bone, or another filler.

In some embodiments, a chain implant 5000 may comprise one or more bodies or beads 5100 having expandable structures 5110, e.g. wings or other structures which may be conical or another desired shape, as shown for example in FIG. 34.

The expandable structures 5110 may comprise a shape memory material, e.g., nickel titanium (Nitinol). For example, a shape memory structure may be configured to expand or otherwise change configuration, e.g., in response to a change in temperature or other stimulus, to provide a "locking" feature for retaining the chain in the vertebrae. In other embodiments, the expandable structures 5110 may comprise other shape memory materials, stainless steel, other metals or metal alloys, a polymer, a ceramic or a composite.

As shown in FIG. 34, wings or other expandable structures 5110 may expand after being ejected from a catheter or other introducer 6000 used to insert the bead chain 5000 into the vertebrae or other bone or cavity. In some embodiments, e.g., shape-memory alloy embodiments, an expandable body, bead or chain of beads or bodies may be "cold-loaded", such that after each body or bead is injected into the vertebral space the warmer body temperature may cause the wings to expand. Alternatively, injection of a warm solution such as warm saline may cause the bodies or beads to expand.

Figure 35A:
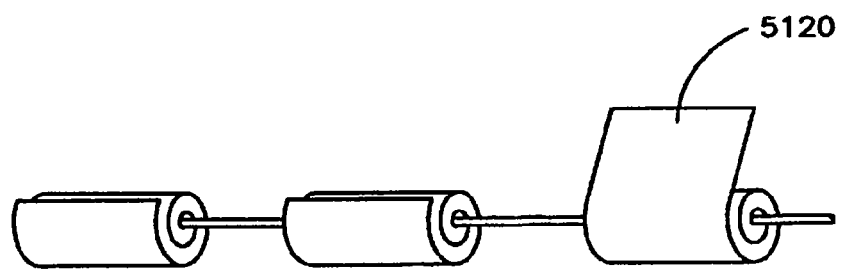
FIG. 35 A-C are side view illustrations of other embodiments of an implant comprising expandable bodies.
Figure 35B:
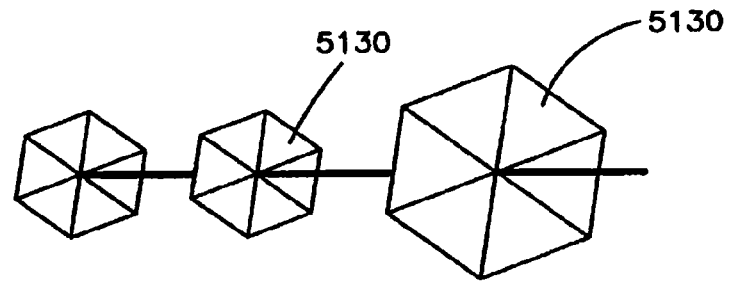

In other embodiments, the expandable beads may comprise coiled or rolled structure 5120, e.g. a ribbon as shown in FIG. 35A, that may unroll or unwind after insertion. Alternatively, as shown in FIG. 35B, one or more beads may comprise compacted struts or legs 5130 that may unfold and/or otherwise expand after insertion into the vertebrae.

Figure 35C:
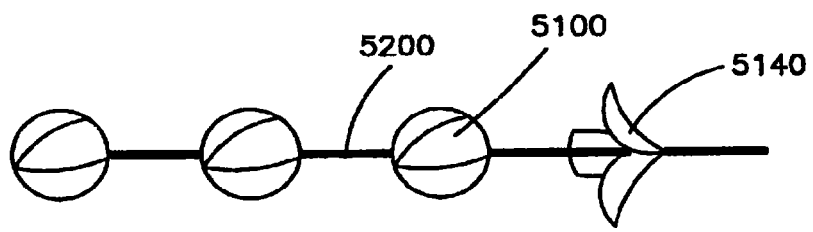

In other embodiments, expandable wings or other structures 5140 may be clipped or otherwise attached to a bead or linking member 5200 between beads 5100, e.g., as shown in FIG. 35C. One or more of such wings or other expandable structures 5140 may be attached during an augmentation procedure. For example, a doctor may insert a desired amount of the bead chain 5000 into the vertebrae, e.g., when the bead chain 5000 has almost filled the capacity of the vertebral body or other bone. At that point, the doctor may attach one or more expandable structures 5140 such as a conical wing on to the chain, e.g., onto one or more beads 5100 that are accessible outside of the insertion device (not shown). After attaching the expandable structure 5140, the doctor may push the remaining bead or beads 5100 through the insertion device until the wings 5140 enter the vertebral body and expand on the other side of the cortical bone opening.

In other embodiments, the wings or other expandable structures on the bead or chain may be expanded by application of a energy source (e.g., an ultraviolet light, ultrasonic radiation, radio waves, heat, electric filed, magnetic field). For example, an expandable wing or other structure may comprise an electroactive polymer that may change shape or other configuration with a small electric current. Alternatively, the beads or bodies may comprise or be coated with a polymer or polymeric cement, which may be porous, that may expand or otherwise change configuration after contact with body fluids, saline, or another fluid or substance that may be present within the implanted area. The activating fluid or substance also may be administered into the implanted area at a desired time before, during or after injection of the beads or bodies. This may allow the beads to expand and lock in place in the vertebrae.

Figure 36A:
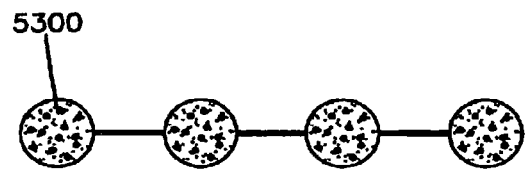
FIGS. 36 A and B are side view illustrations of linked bodies configured to contain a filler material.
Figure 36B:
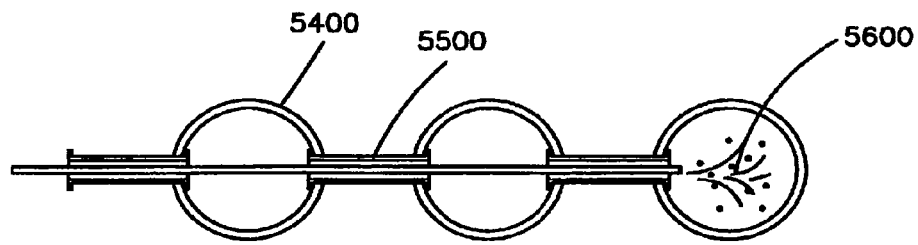

Another alternative to injecting cement with the beads is to utilize bodies or beads 5300 with cement, glue, polymer, or other adhesive or filler inside of the beads, e.g., within a hollow core or other cavity as shown in FIGS. 36A and 36B. For example, the walls of the beads 5300 surrounding the hollow core or cavity may be non-porous, porous or semi-porous. In porous or semi-porous embodiments, for example, the walls may comprise a coating, e.g., a thin coating of a polymer or other suitable material, to retain the adhesive, polymer cement, glue or other filler. As the beads 5300 are injected, the coating may dissolve or the outer shell be collapsed or otherwise altered to allow the adhesive or other filler to escape and lock the bead chain in a desired position.

As shown in FIG. 36B, the beads 5400 and the linking members 5500 or other connectors between the beads 5400 may be hollow such that a microcatheter 6100 or other introducer may be threaded through the beads 5400 and/or linking member 5500, e.g., prior to insertion. After the beads 5400 are injected into the vertebrae, an adhesive 5600 may be injected or otherwise administered into the beads 5400 and chain 5000, e.g., through the microcatheter 6100. The adhesive 5600 or other filler may harden and/or lock the beads 5400 into a desired position. As the adhesive 5600 is being injected into the beads 5400 and/or linking or chain members 5500, the microcatheter 6100 may be withdrawn, e.g., to avoid kinking or other obstruction of the clustered bead chain within the vertebral body.

Expandable bodies and/or chains comprising one or more of such expandable bodies may be incorporated within any of the apparatus and methods described herein, e.g., for augmenting and/or repositioning vertebral bodies or other bones or structures.

D. Other Embodiments

Figures 37A, 37B:
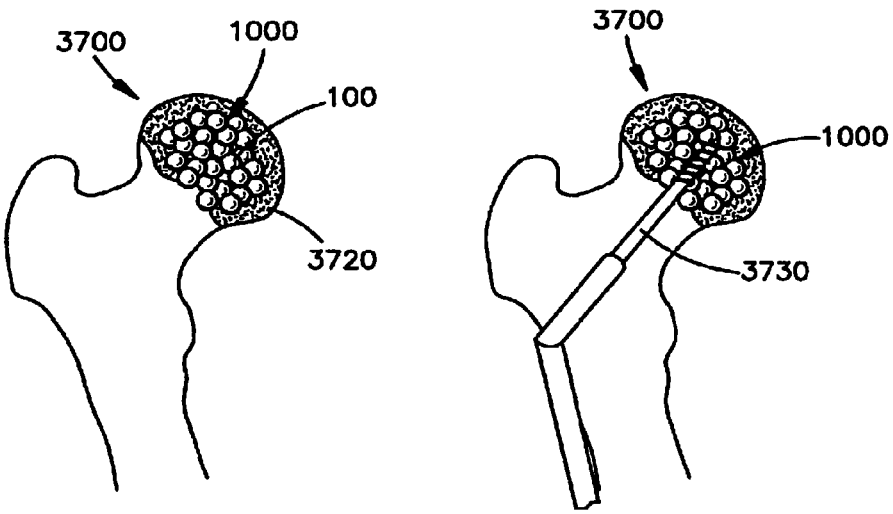
FIG. 37 is a side cross-sectional view illustration of a femur augmented with implants according to an embodiment of the present invention.

Although the apparatus and methods described herein thus far have been described in the context of repositioning and augmenting vertebrae in the context of vertebral compression fractures and deformations in spinal curvature, various other uses and methods are envisioned. For example, in some embodiments, an implantable chain 1000 of linked bodies 100 may be used to reposition and/or augment other damaged bone regions such as a fractured or weak proximal femur 3700 as shown in FIG. 37. In such embodiments, for example, one or more chains 1000 may be inserted into a head 3720 of femur 3700, e.g., through a cannula or other introducer. Once inserted, bodies 100 of chain 1000 may compact material within head 3720 and provide solid support to augment the head 3720. A bone cement or other filler may also be used to aid augmentation. In other embodiments, another implant 3730 may be inserted in addition to or instead of one or more chains 1000.

In some embodiments, the implants and methods described herein may be used in conjunction with other apparatus and methods to restore lordosis and augment vertebral body. For example, one or more chains 1000 or bone anchors 2510 may be used in conjunction with known procedures, e.g., a balloon kyphoplasty, that may be used to begin repositioning of a vertebral body and/or create a space within the body for chain 1000. In other embodiments, chains 1000, anchors 2510, tensioning members 2530 or other elements or devices described herein may be used in conjunction with other tools or external fixation apparatus for helping to manipulate or fix the vertebrae or other bones in a desired position.

In another embodiment, a kit comprises various combinations of assemblies and components may be provided. A kit may include, for example, a cannula and one or more chains 1000 of linked bodies 100 and/or expandable linked bodies according to the present invention. The one or more chains may be provided in different sizes, e.g., different lengths and/or diameters (widths). In other embodiments, a kit may include a cannula and/or sheath, one or more chains, and a syringe or other apparatus for injecting a cement or other filler into a vertebral body. In other embodiments, a kit may comprise one or more anchoring elements, one or more tensioning members, and one or more longitudinal fixation members. Such kit may also include, for example, a syringe or other container of a cement or other bone filler material. One skilled in the art will appreciate that various other combinations of devices, components and assemblies can be made and are intended to fall within the scope of the present invention.

In other embodiments, various minimally invasive implants and methods for alleviating discomfort associated with the spinal column may employ anchors and other implants described herein. For example, an implant comprising one or more linked bodies, for example within an expandable container (not shown), may be implanted between spinous processes of adjacent vertebrae to distract the processes and alleviate pain and other problems caused for example by spinal stenosis, facet arthropathy, and the like. For example, augmentation systems described herein may be used instead of or in addition to expandable interspinous process apparatus and methods described in U.S. Patent Publication number 2004/018128 and U.S. Pat. No. 6,419,676 to Zucherman et al.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. The presently disclosed embodiments are therefore to be considered in all respects as illustrative and not restrictive, the scope of the invention being indicated by the appended claims, and not limited to the foregoing description.

The invention claimed is:

1. A method of repositioning a spine by restoring a desired curvature to the spine and restoring a height to a damaged vertebra comprising the steps of:
   inserting a first end of a first anchoring element into a vertebral body of a first vertebra, wherein the first vertebra is located cranially of a damaged vertebra, and wherein a first end of a first chain is attached to a second end of the first anchoring element, the first chain comprising a plurality of linked bodies;
   inserting a first end of a second anchoring element into a vertebral body of a second vertebra, wherein the second vertebra is located caudally of the damaged vertebra, and wherein a first end of a second chain is attached to a second end of the second anchoring element, the second chain comprising a plurality of linked bodies;
   positioning at least one longitudinal fixation member along a longitudinal axis of the spine, the longitudinal fixation member including first and second slots, wherein the first slot is positioned superior to the second slot on the longitudinal fixation member;
   inserting a second end of the first chain thru the first slot formed in the longitudinal fixation member;
   inserting a second end of the second chain thru the second slot formed in the longitudinal fixation member;
   applying a tensioning force to the first and second chains to reposition the first and second vertebrae away from the damaged vertebra to thus restore curvature to the spine and to restore a height to the damaged vertebra; and
   securing the first and second chains to the longitudinal fixation member to maintain the desired spinal curvature.

2. The method of claim 1, wherein the longitudinal fixation member is a plate.

3. The method of claim 1, wherein each of the first and second slots formed in the longitudinal fixation member has a first dimension configured to allow the first and second chains to be inserted through the first and second slots, respectively, and a second dimension configured to releasably secure the first and second chains in the first and second slots, respectively, and the step of securing the first and second chains to the longitudinal fixation member comprises inserting the second end of the first and second chains thru the first dimension of the first and second slots, respectively, and moving the first and second chains laterally with respect to the longitudinal fixation member so that the second end of the first and second chains is located within the second dimension of the first and second slots, respectively.

4. The method of claim 1, wherein the first anchoring element is a bone screw.

5. The method of claim 4, wherein the bone screw comprises a lumen.

6. The method of claim 1, wherein the linked bodies of each of the first and second chains are joined by linking members.

7. The method of claim 6, wherein the bodies are spherical.

8. The method of claim 6, wherein the bodies are non-spherical.

9. The method of claim 1, wherein the first and second chains are secured to the longitudinal fixation member via slotted holes in the longitudinal fixation member.

10. The method of claim 9, wherein the slotted holes include a passage having a diameter larger than a diameter of the linked bodies of each of the first and second chains.

* * * * *